(12) United States Patent
Noriega et al.

(10) Patent No.: US 6,190,669 B1
(45) Date of Patent: Feb. 20, 2001

(54) ATTENUATED MUTANTS OF SALMONELLA WHICH CONSTITUTIVELY EXPRESS THE VI ANTIGEN

(75) Inventors: Fernando R. Noriega, Baltimore; Marcelo B. Sztein; Myron M. Levine, both of Columbia, all of MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 09/076,761

(22) Filed: May 13, 1998

(51) Int. Cl.$^7$ .................................................. A61K 39/112
(52) U.S. Cl. .................... 424/258.1; 424/93.1; 424/93.2; 424/93.4; 424/93.48; 424/831; 435/879; 935/33; 935/38; 935/41
(58) Field of Search ............................. 424/184.1, 234.1, 424/258.1, 93.1, 93.4, 831, 93.48, 93.2; 935/33, 41, 38; 435/822, 879

(56) References Cited

U.S. PATENT DOCUMENTS

| 5,077,044 | 12/1991 | Stocker | 424/92 |
|---|---|---|---|
| 5,783,196 | 7/1998 | Noriega | 424/234.1 |

OTHER PUBLICATIONS

Robbins et al, *J. Infect. Dis.*, 150 (3):436–449 (1984).
Cryz, Jr. et al, *Infect. Immun.*, 57(12):3863–3868 (1989).
Cao et al, *Infect. Immun.*, 60(7):2823–2827 (1992).
Pickard et al, *Infect. Immun.*, 62(9):3984–3993 (1994).
Noriega et al, *Infect. Immun.*, 64(8)3055–3061 (1996).
McFarland et al, *Microbial Pathogenesis*, 3:129–141 (1987).
Testa–Selase et al, *Mol. Gen. Genet.*, 231:256–264 (1992).
Hosieth et al, *Nature*, 291:238–239 (1981).
Edwards et al, *J. Bacteriol.*, 170(9):3991–3995 (1988).
Levine et al, *J. Clin. Invest.*, 79:888–902 (1987).
Levine et al, *Rev. of Infect. Dis.*, II(3):S552–S567 (1989).
O'Callaghan et al, *Infect. Immun.*, 56(2):419–423 (1988).
Sigwart et al, *Infect. Immun.*, 57(6):1858–1861 (1989).
Murray et al, *J. Bacteriol.*, 175(16):5216–5223 (1993).
Gilbert et al, *Biochem. J.*, 191:533–541 (1980).
Lindberg, *Dev. Biol. Stand. Basel, Karger*, 84:211–219 (1995).
Nataro et al, *Infect. Immun.*, 63(12): 4721–4728 (1995).
Noriega et al, "Construction and Characterization of Oral Attenuated Shigella Vaccine–Candidates and their Potential Use as Live Vector–Hybrid Vaccines", pp. 166–168, Abstracts, 29th Joint Conference on Cholera and Related Diarrheal Diseases (Dec. 23, 1993).
Bacon et al, *Br. J. Exp. Path.*, 31:714–724 (1950).
Karnell et al, *Vaccine*, 11 (8):830–836 (1993).
Verma et al, *Vaccine*, 9:6–9 (1991).
Neidhardt, "*Escherichia coli* and *Salmonella Typhimurium*", Cellular and Molecular Microbiol., Section 29, Purines and Pyrimidines, p. 449 (1987).
Noriega, *Am. Soc. of Microbiol.*, 34:188 (1994).
Pickard et al. Infection and Immunity 62(9):3984–3993, 1994.*
Cryz et al. Infection and Immunity 57(12):3863–3768, 1989.*

* cited by examiner

*Primary Examiner*—Patricia A. Duffy
(74) *Attorney, Agent, or Firm*—Sughrue, Mion, Zinn Macpeak & Seas. PLLC

(57) ABSTRACT

Attenuated Salmonella mutants which constitutively express the Vi antigen are disclosed, as well as vaccines against typhoid fever containing the same, live vector vaccines containing the same, and DNA-mediated vaccines containing the same.

23 Claims, 15 Drawing Sheets

```
                                                              AlwI
                                                               |
GTAAAGTACCAGTGACCGGAAGCTGGTTGCGTGAAATTAGAAATTTCGCCGCTGATCCAA    60
CATTTCATGGTCACTGGCCTTCGACCAACGCACTTTAATCTTTAAAGCGGCGACTAGGTT

HinfI
                                            |
ACCTGTCCCATCTCATGCTCAAGCAGCAGACGAACCGTTTGATTCAGGCGACTAACGGTA   120
TGGACAGGGTAGAGTACGAGTTCGTCGTCTGCTTGGCAAACTAAGTCCGCTGATTGCCAT NspHI
              AflIII                                  BspMI
                |                                       |
AAAATTGCAGGGGATTGAGAAGGTAACATGTGAGCGAGATCAAATTCTAAATCAGCAGGT   180
TTTTAACGTCCCCTAACTCTTCCATTGTACACTCGCTCTAGTTTAAGATTTAGTCGTCCA TATTCAGTCGATAGTAACCCGCCCTTCGGGGATAGCAAGCATTTTTTGCAAAAAGGGGTA   240
ATAAGTCAGCTATCATTGGGCGGGAAGCCCCTATCGTTCGTAAAAAACGTTTTTCCCCAT SfaNI                   SacII   SspI    MseI
 |                        |       |      |
GATGCAATCGGTTACGCTCTGTATAATGCCGCGGCAATATTTATTAACCACTCTGGTCGA   300
CTACGTTAGCCAATGCGAGACATATTACGGCGCCGTTATAAATAATTGGTGAGACCAGCT SnaBI
           |
GATATTGCCCATGCTACGTATCGCTAAAGAAGCTCTGACGTTTGACGACGTTCTCCTCGT   360
CTATAACGGGTACGATGCATAGCGATTTCTTCGAGACTGCAAACTGCTGCAAGAGGAGCA DdeI     PvuII
                                |        |
TCCTGCTCACTCTACCGTTCTGCCGAATACTGCTGACCTCAGCACCCAGCTGACGAAAAC   420
AGGACGAGTGAGATGGCAAGACGGCTTATGACGACTGGAGTCGTGGGTCGACTGCTTTTG EcoRII
                                                         BstNI
                                                BssHII
                                                   |      |
TATTCGTCTGAATATCCCTATGCTTTCCGCAGCAATGGATACCGTAACGGAAGCGCGCCT   480
ATAAGCAGACTTATAGGGATACGAAAGGCGTCGTTACCTATGGCATTGCCTTCGCGCGGA NspHI
              DdeI                                 AflIII
                |                                    |
GGCTATTGCTCTGGCTCAGGAAGGCGGTATCGGCTTTATCCACAAAAACATGTCCATTGA   540
CCGATAACGAGACCGAGTCCTTCCGCCATAGCCGAAATAGGTGTTTTTGTACAGGTAACT
```

FIG. 3A

```
         EcoRII
         BstNI    XmnI                            HinfI               AlwI
         |        |                               |                   |
         ACGCCAGGCAGAAGAAGTTCGCCGTGTGAAAAAACACGAATCTGGTGTGGTGACTGATCC       600
         TGCGGTCCGTCTTCTTCAAGCGGCACACTTTTTTGTGCTTAGACCACACCACTGACTAGG
                         HgaI
                         |
         GCAGACTGTTCTGCCAACCACGACGCTGCGCGAAGTGAAAGAACTGACCGAGCGTAACGG       660
         CGTCTGACAAGACGGTTGGTGCTGCGACGCGCTTCACTTTCTTGACTGGCTCGCATTGCC
                                                                Cfr10I
                                                                |
         TTTTGCGGGCTATCCGGTCGTTACCGAAGAAAACGAACTGGTGGGTATTATCACCGGTCG       720
         AAAACGCCCGATAGGCCAGCAATGGCTTCTTTTGCTTGACCACCCATAATAGTGGCCAGC
                                                             HgaI
                                    Cfr10I                   AhaII
                                    |                        |
         TGACGTGCGTTTTGTTACCGACCTGAACCAGCCGGTTAGCGTTTACATGACGCCGAAAGA       780
         ACTGCACGCAAAACAATGGCTGGACTTGGTCGGCCAATCGCAAATGTACTGCGGCTTTCT
         HgaI BstEII
         |    |
         GCGTCTGGTCACCGTGCGTGAAGGTGAAGCCCGTGAAGTGGTGCTGGCAAAAATGCACGA       840
         CGCAGACCAGTGGCACGCACTTCCACTTCGGGCACTTCACCACGACCGTTTTTACGTGCT
         MluI       HaeII
         AflIII     Eco47III        EcoRI                BclI
         |          |               |                    |
         AAAACGCGTTGAAAAAGCGCTGGTGGTTGATGACGAATTCCACCTGATCGGCATGATCAC       900
         TTTTGCGCAACTTTTTCGCGACCACCAACTACTGCTTAAGGTGGACTAGCCGTACTAGTG
         XmnI
         |
         CGTGAAAGACTTCCAGAAAGCGGAAGCTAAACCGAACGCCTGTAAAGACGAGCAAGGCCG       960
         GCACTTTCTGAAGGTCTTTCGCCTTCGATTTGGCTTGCGGACATTTCTGCTCGTTCCGGC
                                                              HgaI
                      BspMI                               HincII
                      |                                   |   |
         TCTGCGTGTTGGTGCAGCGGTTGGCGCAGGTGCGGGTAACGAAGAGCGTGTTGACGCGCT      1020
         AGACGCACAACCACGTCGCCAACCGCGTCCACGCCCATTGCTTCTCGCACAACTGCGCGA
                               PleI
                  HincII       HinfI               DdeI
                  |            |                   |
         GGTTGCCGCAGGCGTTGACGTTCTGCTGATCGACTCCTCCCACGGTCACTCAGAAGGTGT      1080
         CCAACGGCGTCCGCAACTGCAAGACGACTAGCTGAGGAGGGTGCCAGTGAGTCTTCCACA
                                         XhoII
                                         AlwI
                                         BspMII
                                         AccIII
                                         |  |
         ACTGCAACGTATCCGTGAAACCCGTGCTAAATATCCGGATCTGCAAATTATCGGCGGCAA      1140
         TGACGTTGCATAGGCACTTTGGGCACGATTTATAGGCCTAGACGTTTAATAGCCGCCGTT
```

FIG. 3B

```
             HgiAI
      BspMI
      PstI   Bsp1286
   PvuII  ApaL1                  AlwNI                       MseI
     | |   |    |                  |                           |
CGTGGCAACAGCTGCAGGTGCACGCGCTCTGGCAGAAGCTGGTTGCAGTGCGGTTAAAGT  1200
GCACCGTTGTCGACGTCCACGTGCGCGAGACCGTCTTCGACCAACGTCACGCCAATTTCA

EcoRII
      BstNI
    Sau96I
    Cfr13I                                        HgaI
    AsuI                                          AhaII
     | |                                           ||
CGGCATTGGCCCTGGCTCTATCTGTACAACTCGTATCGTGACTGGCGTCGGTGTTCCGCA  1260
GCCGTAACCGGGACCGAGATAGACATGTTGAGCATAGCACTGACCGCAGCCACAAGGCGT

Cfr10I
                              EcoRII NlaIV
                HgaI          BstNI  BanI
                 |              |     |
GATTACCGCTGTTGCTGACGCAGTAGAAGCCCTGGAAGGCACCGGTATTCCGGTTATCGC  1320
CTAATGGCGACAACGACTGCGTCATCTTCGGGACCTTCCGTGGCCATAAGGCCAATAGCG

TGATGGCGGTATTCGCTTCTCCGGCGACATCGCCAAAGCTATCGCCGCTGGCGCAAGCGC  1380
ACTACCGCCATAAGCGAAGAGGCCGCTGTAGCGGTTTCGATAGCGGCGACCGCGTTCGCG

NciI
      NlaIV                         HinfI BcnI
        |                             |    |
GGTGATGGTAGGTTCCATGCTGGCGGGTACTGAAGAATCTCCGGGTGAAATCGAACTCTA  1440
CCACTACCATCCAAGGTACGACCGCCCATGACTTCTTAGAGGCCCACTTTAGCTTGAGAT Sau96I
   Cfr13I
    AsuI                             EcoRII
EcoRII                               BstNI
BstNI                          NlaIV                     NlaIV
 | |                             |    |                    |
CCAGGGCCGTTCTTACAAATCTTACCGTGGTATGGGTTCCCTGGGCGCGATGTCCAAAGG  1500
GGTCCCGGCAAGAATGTTTAGAATGGCACCATACCCAAGGGACCCGCGCTACAGGTTTCC NlaIV
                                                BanI
                                                  |
TTCCTCTGACCGTTATTTCCAGAGCGATAACGCTGCCGACAAACTGGTGCCGGAAGGTAT  1560
AAGGAGACTGGCAATAAAGGTCTCGCTATTGCGACGGCTGTTTGACCACGGCCTTCCATA PflMI
                                                |
CGAAGGTCGCGTAGCCTATAAAGGTCGCCTGAAAGAGATCATTCACCAGCAGATGGGCGG  1620
GCTTCCAGCGCATCGGATATTTCCAGCGGACTTTCTCTAGTAAGTGGTCGTCTACCCGCC Cfr10I
                 |
CCTGCGCTCCTGTATGGGTCTGACCGGCTGTGGTACTATCGACGAACTGCGTACTAAAGC  1680
GGACGCGAGGACATACCCAGACTGGCCGACACCATGATAGCTGCTTGACGCATGATTTCG
```

FIG. 3C

```
              SnaBI              BsmI                    DraIII
                |                  |                       |
GGAGTTTGTACGTATCAGCGGTGCGGGCATTCAGGAAAGCCACGTTCACGACGTGACCAT   1740
CCTCAAACATGCATAGTCGCCACGCCCGTAAGTCCTTTTCGGTGCAAGTGCTGCACTGGTA
                         NlaIV
   PleI                  Bsp1286
   HinfI                 BanII      HinfI
     |                    ||          |
TACTAAAGAGTCCCCGAACTACCGTCTGGGCTCCTGATTCTCTTCGCCCGACTTCATGTC   1800
ATGATTTCTCAGGGGCTTGATGGCAGACCCGAGGACTAAGAGAAGCGGGCTGAAGTACAG
                                HgaI            XmnI
                                  |                |
GGGCGATTTATATTATCTGTTTCACTTGCCTCGGAATAAGCGTCAATGACGGAAAACATT   1860
CCCGCTAAATATAATAGACAAAGTGAACGGAGCCTTATTCGCAGTTACTGCCTTTTGTAA
            SfaNI
   SfaNI    FokI                DdeI                     BssHII
     |       ||                   |                        |
CATAAGCATCGCATCCTCATTCTGGACTTCGGTTCTCAGTACACTCAACTGGTTGCGCGC   1920
GTATTCGTAGCGTAGGAGTAAGACCTGAAGCCAAGAGTCATGTGAGTTGACCAACGCGCG
                                         FokI
                                           |
CGCGTGCGTGAGCTGGGTGTTTACTGCGAACTGTGGGCGTGGGATGTGACAGAAGCACAA   1980
GCGCACGCACTCGACCCACAAATGACGCTTGACACCCGCACCCTACACTGTCTTCGTGTT
                                              NciI
                                              BcnI
                                              Sau96I
                                              Cfr13I
                                              AsuI         ScaI
                                                ||           |
ATTCGTGACTTCAATCCAAGCGGCATTATTCTTTCCGGCGGCCCGGAAAGTACTACTGAA   2040
TAAGCACTGAAGTTAGGTTCGCCGTAATAAGAAAGGCCGCCGGGCCTTTCATGATGACTT
                                    Cfr10I
                                      |
GAAAACAGTCCGCGTGCGCCGCAGTATGTCTTTGAAGCAGGCGTACCGGTATTCGGCGTT   2100
CTTTTGTCAGGCGCACGCGGCGTCATACAGAAACTTCGTCCGCATGGCCATAAGCCGCAA
   SphI     StyI
   NspHI    NcoI
     |       |
TGCTATGGCATGCAGACCATGGCAATGCAGTTGGGCGGTCACGTTGAAGCCTCTAACGAA   2160
ACGATACCGTACGTCTGGTACCGTTACGTCAACCCGCCAGTGCAACTTCGGAGATTGCTT
            BspMI
              |
CGTGAATTTGGCTACGCGCAGGTTGAAGTCGTAAACGACAGCGCACTGGTTCGCGGTATC   2220
GCACTTAAACCGATGCGCGTCCAACTTCAGCATTTGCTGTCGCGTGACCAAGCGCCATAG
   SfaNI                                     FokI
     |                                         |
GAAGATGCGCTGACCGCAGACGGTAAACCGCTGCTCGATGTCTGGATGAGCCACGGCGAT   2280
CTTCTACGCGACTGGCGTCTGCCATTTGGCGACGAGCTACAGACCTACTCGGTGCCGCTA
```

FIG. 3D

```
AAAGTTACCGCTATTCCGTCCGACTTCATCACCGTAGCCAGCACCGAAAGCTGCCCGTTT     2340
TTTCAATGGCGATAAGGCAGGCTGAAGTAGTGGCATCGGTCGTGGCTTTCGACGGGCAAA
                                              NciI     PleI
BglI                                          BcnI     HinfI
 |                                             |        |
GCCATTATGGCTAACGAAGAAAAACGCTTCTATGGCGTACAGTTCCACCCGGAAGTGACT     2400
CGGTAATACCGATTGCTTCTTTTTGCGAAGATACCGCATGTCAAGGTGGGCCTTCACTGA
                SphI
                NspHI
     EcoRII FspI
     BstNI  AosI                       EcoRV
       |    | |                          |
CATACCCGCCAGGGTATGCGCATGCTGGAGCGTTTTGTGCGTGATATCTGCCAGTGTGAA     2460
GTATGGGCGGTCCCATACGCGTACGACCTCGCAAAACACGCACTATAGACGGTCACACTT
     HgaI                           FokI
     AhaII              SfaNI       SfaNI        BspMI
       |                  |          | |           |
GCCCTGTGGACGCCAGCGAAAATTATCGACGATGCTGTAGCTCGCATCCGCGAGCAGGTA     2520
CGGGACACCTGCGGTCGCTTTTAATAGCTGCTACGACATCGAGCGTAGGCGCTCGTCCAT
          FokI                    HinfI
           |                        |
GGCGACGATAAAGTCATCCTCGGCCTCTCTGGTGGTGTGGATTCCTCCGTAACCGCAATG     2580
CCGCTGCTATTTCAGTAGGAGCCGGAGAGACCACCACACCTAAGGAGGCATTGGCGTTAC
                                   SalI
                                   HincII
                                   AccI
                                     |
CTGCTGCACCGCGCTATCGGTAAAAACCTGACTTGCGTATTCGTCGACAACGGCCTGCTG     2640
GACGACGTGGCGCGATAGCCATTTTTGGACTGAACGCATAAGCAGCTGTTGCCGGACGAC
          AlwNI
          BspMI                                   MseI
          | |                                       |
CGCCTCAACGAAGCAGAGCAGGTTCTGGATATGTTTGGCGATCACTTTGGTCTTAACATT     2700
GCGGAGTTGCTTCGTCTCGTCCAAGACCTATACAAACCGCTAGTGAAACCAGAATTGTAA
                                                    BspMII
                           HaeII                    AccIII
       Cfr10I               Eco47III                AlwI
         |                     |                    | |
GTTCACGTACCGGCAGAAGATCGCTTCCTGTCAGCGCTGGCTGGCGAAAACGATCCGGAA     2760
CAAGTGCATGGCCGTCTTCTAGCGAAGGACAGTCGCGACCGACCGCTTTTGCTAGGCCTT
```

FIG. 3E

```
                                                        HaeII
                                                        Eco47III
                                                        |
GCAAAACGTAAAATCATCGGTCGCGTTTTCGTTGAAGTATTCGATGAAGAAGCGCTGAAA    2820
CGTTTTGCATTTTAGTAGCCAGCGCAAAAGCAACTTCATAAGCTACTTCTTCGCGACTTT

NlaIV
                            BanI
                            Bsp1286              HinfI    AhaII
                            | |                  |        |
CTGGAAGACGTGAAGTGGCTGGCGCAGGGCACCATCTACCCTGACGTTATCGAATCTGCG    2880
GACCTTCTGCACTTCACCGACCGCGTCCCGTGGTAGATGGGACTGCAATAGCTTAGACGC DraIII
HgaI    Cfr10I     AflIII               PflMI
|       |          |                    ||
GCGTCTGCAACCGGTAAAGCACACGTCATCAAATCTCACCACAACGTGGGCGGCCTGCCG    2940
CGCAGACGTTGGCCATTTCGTGTGCAGTAGTTTAGAGTGGTGTTGCACCCGCCGGACGGC EcoRII
           BstNI
         Sau96I
         EaeI
         Cfr13I
         AsuI
         | |
AAAGAGATGAAGATGGGCCTGGTTGAACCGCTGAAAGAGCTGTTCAAAGACGAAGTGCGT    3000
TTTCTCTACTTCTACCCGGACCAACTTGGCGACTTTCTCGACAAGTTTCTGCTTCACGCA Sau96I
                                                        Cfr13I
                                                        AvaII
                                                        AsuI
                                                        NlaIV
                                                        NciI
                                                        BcnI
                                                        XmaI
                      Sau96I                            SmaI
                      EaeI                              NciI
                      Cfr13I                            BcnI
                      AsuI    SplI  NspHI               AvaI
                      |       |     |                   || ||
AAGATTGGTCTGGAGCTGGGCCTGCCGTACGACATGCTGTACCGTCACCCGTTCCCGGGA    3060
TTCTAACCAGACCTCGACCCGGACGGCATGCTGTACGACATGGCAGTGGGCAAGGGCCCT
```

FIG. 3F

```
      StyI
    StuI
    EaeI
  PflMI
  EcoRII
  BstNI                                    ScaI        BspMI
  | | |                                     |            |
CCAGGCCTTGGCGTTCGTGTTCTGGGTGAAGTGAAGAAAGAGTACTGTGACCTGCTGCGC   3120
GGTCCGGAACCGCAAGCACAAGACCCACTTCACTTCTTTCTCATGACACTGGACGACGCG

Sau96I
                                Cfr13I
        HgaI                    AvaII                        EcoRII
        AhaII                   AsuI        Tth111I          BstNI
        |                         |            |               |
CGTGCTGACGCCATCTTCATTGAAGAACTGCGTAAAGCGGACCTGTACGACAAAGTCAGC   3180
GCACGACTGCGGTAGAAGTAACTTCTTGACGCATTTCGCCTGGACATGCTGTTTCAGTCG

Cfr10I
                |
CAGGCGTTCACTGTGTTCCTGCCGGTACGTTCCGTTGGCGTAATGGGCGATGGTCGTAAG   3240
GTCCGCAAGTGACACAAGGACGGCCATGCAAGGCAACCGCATTACCCGCTACCAGCATTC

TATGACTGGGTTGTCTCTCTGCGTGCTGTCGAAACCATCGACTTTATGACCGCACACTGG   3300
ATACTGACCCAACAGAGAGACGCACGACAGCTTTGGTAGCTGAAATACTGGCGTGTGACC

SfaNI    SplI
    |         |
GCGCATCTGCCGTACGATTTCCTCGGTCGCGTTTCCAACCGCATTATCAATGAAGTGAAC   3360
CGCGTAGACGGCATGCTAAAGGAGCCAGCGCAAAGGTTGGCGTAATAGTTACTTCACTTG

PflMI
                                                 |
GGTATTTCCCGCGTGGTGTATGACATCAGCGGCAAGCCGCCAGCTACCATTGAGTGGGAA   3420
CCATAAAGGGCGCACCACATACTGTAGTCGCCGTTCGGCGGTCGATGGTAACTCACCCTT

TGATTTGACCCTGCACTATGAATGAACAAAACCCTCTGTTACTACAGAGGGTTTTTTATC   3480
ACTAAACTGGGACGTGATACTTACTTGTTTTGGGAGACAATGATGTCTCCCAAAAAATAG

AseI MseI
                ClaI MseI      PvuII
                  |   | |       |
TTCAAGAATTATAGGATTGAAGTTACTAACATCGATTAATTAAACCAGCTG            3531
AAGTTCTTAATATCCTAACTTCAATGATTGTAGCTAATTAATTTGGTCGAC
```

FIG. 3G

*RECIPROCAL GEOMETRIC MEAN TITER±SD

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 3531 base pairs
       (B) TYPE: nucleic acid
       (C) STRANDEDNESS: single
       (D) TOPOLOGY: linear (ii) MOLECULE TYPE: genomic DNA (iii) HYPOTHETICAL: NO (iv) ANTI-SENSE: NO (xi) SEQUENCE DESCRIPTION: SEQ ID NO:1:

```
GTAAAGTACC AGTGACCGGA AGCTGGTTGC GTGAAATTAG AAATTTCGCC GCTGATCCAA      60
ACCTGTCCCA TCTCATGCTC AAGCAGCAGA CGAACCGTTT GATTCAGGCG ACTAACGGTA     120
AAAATTGCAG GGGATTGAGA AGGTAACATG TGAGCGAGAT CAAATTCTAA ATCAGCAGGT     180
TATTCAGTCG ATAGTAACCC GCCCTTCGGG GATAGCAAGC ATTTTTTGCA AAAGGGGTA     240
GATGCAATCG GTTACGCTCT GTATAATGCC GCGGCAATAT TTATTAACCA CTCTGGTCGA     300
GATATTGCCC ATGCTACGTA TCGCTAAAGA AGCTCTGACG TTTGACGACG TTCTCCTCGT     360
TCCTGCTCAC TCTACCGTTC TGCCGAATAC TGCTGACCTC AGCACCCAGC TGACGAAAAC     420
TATTCGTCTG AATATCCCTA TGCTTTCCGC AGCAATGGAT ACCGTAACGG AAGCGCGCCT     480
GGCTATTGCT CTGGCTCAGG AAGGCGGTAT CGGCTTTATC CACAAAAACA TGTCCATTGA     540
ACGCCAGGCA GAAGAAGTTC GCCGTGTGAA AAAACACGAA TCTGGTGTGG TGACTGATCC     600
GCAGACTGTT CTGCCAACCA CGACGCTGCG CGAAGTGAAA GAACTGACCG AGCGTAACGG     660
TTTTGCGGGC TATCCGGTCG TTACCGAAGA AAACGAACTG GTGGGTATTA TCACCGGTCG     720
TGACGTGCGT TTTGTTACCG ACCTGAACCA GCCGGTTAGC GTTTACATGA CGCCGAAAGA     780
GCGTCTGGTC ACCGTGCGTG AAGGTGAAGC CCGTGAAGTG GTGCTGGCAA AAATGCACGA     840
AAAACGCGTT GAAAAAGCGC TGGTGGTTGA TGACGAATTC CACCTGATCG GCATGATCAC     900
CGTGAAAGAC TTCCAGAAAG CGGAAGCTAA ACCGAACGCC TGTAAAGACG AGCAAGGCCG     960
TCTGCGTGTT GGTGCAGCGG TTGGCGCAGG TGCGGGTAAC GAAGAGCGTG TTGACGCGCT    1020
GGTTGCCGCA GGCGTTGACG TTCTGCTGAT CGACTCCTCC CACGGTCACT CAGAAGGTGT    1080
ACTGCAACGT ATCCGTGAAA CCCGTGCTAA ATATCCGGAT CTGCAAATTA TCGGCGGCAA    1140
CGTGGCAACA GCTGCAGGTG CACGCGCTCT GGCAGAAGCT GGTTGCAGTG CGGTTAAAGT    1200
CGGCATTGGC CCTGGCTCTA TCTGTACAAC TCGTATCGTG ACTGGCGTCG GTGTTCCGCA    1260
GATTACCGCT GTTGCTGACG CAGTAGAAGC CCTGGAAGGC ACCGGTATTC CGGTTATCGC    1320
TGATGGCGGT ATTCGCTTCT CCGGCGACAT CGCCAAAGCT ATCGCCGCTG GCGCAAGCGC    1380
GGTGATGGTA GGTTCCATGC TGGCGGGTAC TGAAGAATCT CCGGGTGAAA TCGAACTCTA    1440
CCAGGGCCGT TCTTACAAAT CTTACCGTGG TATGGGTTCC CTGGGCGCGA TGTCCAAAGG    1500
TTCCTCTGAC CGTTATTTCC AGAGCGATAA CGCTGCCGAC AAACTGGTGC CGGAAGGTAT    1560
CGAAGGTCGC GTAGCCTATA AGGTCGCCT GAAAGAGATC ATTCACCAGC AGATGGGCGG    1620
CCTGCGCTCC TGTATGGGTC TGACCGGCTG TGGTACTATC GACGAACTGC GTACTAAAGC    1680
```

-continued

```
GGAGTTTGTA CGTATCAGCG GTGCGGGCAT TCAGGAAAGC CACGTTCACG ACGTGACCAT    1740

TACTAAAGAG TCCCCGAACT ACCGTCTGGG CTCCTGATTC TCTTCGCCCG ACTTCATGTC    1800

GGGCGATTTA TATTATCTGT TTCACTTGCC TCGGAATAAG CGTCAATGAC GGAAAACATT    1860

CATAAGCATC GCATCCTCAT TCTGGACTTC GGTTCTCAGT ACACTCAACT GGTTGCGCGC    1920

CGCGTGCGTG AGCTGGGTGT TTACTGCGAA CTGTGGGCGT GGGATGTGAC AGAAGCACAA    1980

ATTCGTGACT TCAATCCAAG CGGCATTATT CTTTCCGGCG GCCCGGAAAG TACTACTGAA    2040

GAAAACAGTC CGCGTGCGCC GCAGTATGTC TTTGAAGCAG GCGTACCGGT ATTCGGCGTT    2100

TGCTATGGCA TGCAGACCAT GGCAATGCAG TTGGGCGGTC ACGTTGAAGC CTCTAACGAA    2160

CGTGAATTTG GCTACGCGCA GGTTGAAGTC GTAAACGACA GCGCACTGGT TCGCGGTATC    2220

GAAGATGCGC TGACCGCAGA CGGTAAACCG CTGCTCGATG TCTGGATGAG CCACGGCGAT    2280

AAAGTTACCG CTATTCCGTC CGACTTCATC ACCGTAGCCA GCACCGAAAG CTGCCCGTTT    2340

GCCATTATGG CTAACGAAGA AAAACGCTTC TATGGCGTAC AGTTCCACCC GGAAGTGACT    2400

CATACCCGCC AGGGTATGCG CATGCTGGAG CGTTTTGTGC GTGATATCTG CCAGTGTGAA    2460

GCCCTGTGGA CGCCAGCGAA AATTATCGAC GATGCTGTAG CTCGCATCCG CGAGCAGGTA    2520

GGCGACGATA AAGTCATCCT CGGCCTCTCT GGTGGTGTGG ATTCCTCCGT AACCGCAATG    2580

CTGCTGCACC GCGCTATCGG TAAAAACCTG ACTTGCGTAT TCGTCGACAA CGGCCTGCTG    2640

CGCCTCAACG AAGCAGAGCA GGTTCTGGAT ATGTTTGGCG ATCACTTTGG TCTTAACATT    2700

GTTCACGTAC CGGCAGAAGA TCGCTTCCTG TCAGCGCTGG CTGGCAAAAA CGATCCGGAA    2760

GCAAAACGTA AAATCATCGG TCGCGTTTTC GTTGAAGTAT TCGATGAAGA AGCGCTGAAA    2820

CTGGAAGACG TGAAGTGGCT GGCGCAGGGC ACCATCTACC CTGACGTTAT CGAATCTGCG    2880

GCGTCTGCAA CCGGTAAAGC ACACGTCATC AAATCTCACC ACAACGTGGG CGGCCTGCCG    2940

AAAGAGATGA AGATGGGCCT GGTTGAACCG CTGAAAGAGC TGTTCAAAGA CGAAGTGCGT    3000

AAGATTGGTC TGGAGCTGGG CCTGCCGTAC GACATGCTGT ACCGTCACCC GTTCCCGGGA    3060

CCAGGCCTTG GCGTTCGTGT TCTGGGTGAA GTGAAGAAAG AGTACTGTGA CCTGCTGCGC    3120

CGTGCTGACG CCATCTTCAT TGAAGAACTG CGTAAAGCGG ACCTGTACGA CAAAGTCAGC    3180

CAGGCGTTCA CTGTGTTCCT GCCGGTACGT TCCGTTGGCG TAATGGGCGA TGGTCGTAAG    3240

TATGACTGGG TTGTCTCTCT GCGTGCTGTC GAAACCATCG ACTTTATGAC CGCACACTGG    3300

GCGCATCTGC CGTACGATTT CCTCGGTCGC GTTTCCAACC GCATTATCAA TGAAGTGAAC    3360

GGTATTTCCC GCGTGGTGTA TGACATCAGC GGCAAGCCGC CAGCTACCAT TGAGTGGGAA    3420

TGATTTGACC CTGCACTATG AATGAACAAA ACCCTCTGTT ACTACAGAGG GTTTTTTATC    3480

TTCAAGAATT ATAGGATTGA AGTTACTAAC ATCGATTAAT TAAACCAGCT G             3531
```

(2) INFORMATION FOR SEQ ID NO:2:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:2:

```
CGAGCTCGCG AGCTCGGTAA AGTACCAGTG ACCGGAAGCT GGTTGCGT                   48
```

(2) INFORMATION FOR SEQ ID NO:3:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:3:

```
GGGCCCGGGG GATCCTCAAC CGACGCCAGT CACGATACGA GTTGTACAGA T         51
```

(2) INFORMATION FOR SEQ ID NO:4:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:4:

```
TGAGGATCCC CCGGGCCCGG CTACGCGCAG GTTGAAGTCG TAAACGACAG C         51
```

(2) INFORMATION FOR SEQ ID NO:5:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:5:

```
GCTCTAGAGC TCTAGAGCTC ATTCCCACTC AATGGTAGCT GGCGGCTT            48
```

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:6:

```
GGGCGGCCTG CGCTCCTGTA TGGGTCTGAC CGGCTGTGGT                     40
```

(2) INFORMATION FOR SEQ ID NO:7:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:7:

GGGGGAGCTC AATTCTGCAA ACCAGCCCTG TACCATCAAG TTCATA                    46

(2) INFORMATION FOR SEQ ID NO:8:

(i) SEQUENCE CHARACTERISTICS:
           (A) LENGTH: 50 base pairs
           (B) TYPE: nucleic acid
           (C) STRANDEDNESS: single
           (D) TOPOLOGY: linear (ii) MOLECULE TYPE: DNA (iii) HYPOTHETICAL: NO (xi) SEQUENCE DESCRIPTION: SEQ ID NO:8:

CCTCATCCCG GGCCCGGATC CACCTGCACA ATTCATTGTT TGTACCTATC                50

(2) INFORMATION FOR SEQ ID NO:9:

(i) SEQUENCE CHARACTERISTICS:
           (A) LENGTH: 57 base pairs
           (B) TYPE: nucleic acid
           (C) STRANDEDNESS: single
           (D) TOPOLOGY: linear (ii) MOLECULE TYPE: DNA (iii) HYPOTHETICAL: NO (xi) SEQUENCE DESCRIPTION: SEQ ID NO:9:

GCAGGTGGAT CCGGGCCCGG GATGAGGTTT CATCATTTCT GGCCTCCGAA                50

TGATATC                                                              57

(2) INFORMATION FOR SEQ ID NO:10:

(i) SEQUENCE CHARACTERISTICS:
           (A) LENGTH: 57 base pairs
           (B) TYPE: nucleic acid
           (C) STRANDEDNESS: single
           (D) TOPOLOGY: linear (ii) MOLECULE TYPE: DNA (iii) HYPOTHETICAL: NO (xi) SEQUENCE DESCRIPTION: SEQ ID NO:10:

ATCCTTGAAT TCGGGGATC CTACTAAAAT TTTATATTTA CAAAGTTAAT                 50

TCTAGGT                                                              57

ATTENUATED MUTANTS OF SALMONELLA WHICH CONSTITUTIVELY EXPRESS THE VI ANTIGEN

The development of the present invention was supported by the University of Maryland, Baltimore, Md. and by funding from the National Institutes of Health under contract numbers AI29471, AI36525, AI40261, and AI45251. The United States Government has a non-exclusive, irrevocable, paid-up license to practice or have practiced for or on behalf of the United States the invention herein as provided for by the terms of the above mentioned contracts awarded by the United States Government.

FIELD OF THE INVENTION

The present invention relates to attenuated Salmonella mutants which constitutively express the Vi antigen, as well as vaccines against typhoid fever containing the same, live vector vaccines containing the same, and DNA-mediated vaccines containing the same.

BACKGROUND OF THE INVENTION

I. The Vi Antigen

The Vi antigen, a capsular polysaccharide, was first described by Felix et al, *Lancet*, 227:186–191 (1934). This capsular polysaccharide is present in Salmonella, such as *S. typhi*, *S. paratyphi* C, and *S. dublin*, as well as in *Citrobacter freundii*. Structurally, the Vi antigen is a linear polymer of β-4,2-deoxy-2N-acetylgalacturonic acid with variable O-acetylation (Daniels et al, *Infect. Immun.*, 57:3159–3164 (1989)). Its presence in *S. typhi* has been correlated, in vitro, with a significant decrease in lysis by serum, complement activation and phagocytosis (Looney et al, *J. Lab. Clin. Med.*, 108:506–516 (1986)). Thus, the Vi antigen may act as a shield protecting *S. typhi* against the immune system.

A. The viaB Chromosomal Region and the Regulation of Expression of the Vi Antigen Three widely separated chromosomal loci, viaA, viaB, and ompB are thought to be necessary for expression of the Vi antigen (Johnson et al, *J. Bacteriol.*, 90:302–308 (1965); and Snellings et al, *J. Bacteriol.*, 145:1010–1017 (1981)). Of these, the viaB locus is always found in Vi antigen-positive strains, and is thought to contain the genes encoding the enzymes necessary for the synthesis of Vi (Hashimoto et al, *J. Bacteriol.*, 175:4456–4465 (1993); and Virlogeux et al, *Microbiol.*, 141:3039–3047 (1995)). The viaB locus consists of 11 open reading frames (ORF) (FIG. 1A), of which the vipA and vipB genes encode the enzymes that synthesize the nucleotide sugar of the Vi polysaccharide, and the five vex genes (vexA–E) are thought to be responsible for translocation of the Vi antigen (Hashimoto et al (1993), supra). The first ORF of the viaB region, i.e., vipR (FIG. 1A), is a positive transcriptional regulator for its own expression, as well as for the expression of vipA, vipB, orf4, vipC, and perhaps others genes downstream of vipR (Hashimoto et al, *J. Bacteriol.*, 178:1430–1436 (1996)). Furthermore, the promoter upstream of vipR also controls the transcription of (at least) vipA and vipB (encoding structural units of the Vi antigen), forming an operon within the viaB region. Another chromosomal region, the ompB operon, comprising the ompR-envZ genes, plays a role in the expression of the Vi antigen as a transcriptional regulator of viaB (Pickard et al, *Infect. Immun.*, 62:3984–3993 (1994)). The ompR-envZ region forms part of the adaptive response of *E. coli* to conditions of high osmolarity. In *S. typhi*, the Vi antigen is osmotically regulated and ompR is necessary for its expression (Pickard et al, supra).

B. Relationship Between Exposure of the Vi Antigen and Immunoprotection

The Vi capsular polysaccharide of *S. typhi* is a virulence factor and a protective antigen in humans (Felix et al (1934), supra). Purified Vi polysaccharide is a licensed parenteral typhoid vaccine that elicits a moderate degree of protective immunity following inoculation with a single dose, and protection is mediated by serum IgG antibodies (Acharya et al, *New England Journal of Medicine*, 317:1101–1104 (1987); and Klugman et al, *Lancet*, 2:1165–1169 (1987)). In contrast, while attenuated *S. typhi* strain Ty21a, a licensed live oral vaccine, does not express the Vi antigen, nor does it elicit serum Vi antibody; nevertheless, Ty21a confers at least moderate levels of protection (Wahdan et al, *J. Infect. Dis.*, 145:292–296 (1982); and Levine et al, *Lancet*, 1:1049–1052 (1987a)). It is believed that cell-mediated immune mechanisms mediate protection in this situation. Several new attenuated strains of *S. typhi* that express the Vi antigen in vitro have failed to elicit serum Vi antibodies when administered as oral vaccines, even though they elicit high titers of O and H antibodies (Tacket et al, *J. Infect. Dis.*, 163:901–904 (1991); Tacket et al, *Vaccine*, 10:443–446 (1992a); and Tacket et al, *Infect. Immun.*, 65:452–456 (1997)). The likely explanation for this phenomenon is that the expression of the Vi antigen is highly regulated in relation to osmotic stimuli (Pickard et al, supra). The supposition is that Vi antigen expression is interrupted, except when the bacteria are extracellular in the blood or other body fluids (e.g., bile).

It was postulated in the present invention that if Vi antigen expression is made constitutive, this would result in the stimulation of serum IgG Vi antibodies, thereby enhancing the overall protection against typhoid fever. It was also postulated in the present invention, that constitutive expression would improve the immune responses to foreign antigens expressed by attenuated Salmonella live vector vaccines and DNA-mediated vaccines.

II. Target Populations of Typhoid Fever

Typhoid fever is exceedingly uncommon in modern industrialized countries where populations have access to treated, bacteriologically-monitored water supplies, and sanitation that removes human fecal waste. In contrast, in less-developed countries, among populations lacking such amenities, typhoid fever is often endemic, and from the public health perspective, typically constitutes the most important enteric disease problem of school age children (Levine et al, *Pediatr. Infect. Dis. J.*, 8:374–381 (1989a)). Systematic clinical, epidemiologic and bacteriologic surveillance for typhoid fever in relation to field trials of candidate vaccines has established, with great accuracy, the incidence of typhoid fever in many populations (Levine et al, *Lancet*, 336:891–894 (1990); Black et al, *Vaccine*, 8:81–84 (1990); Levine et al . (1987a), supra; Ferreccio et al, *J. Infect. Dis.*, 159:766–769 (1989); and Simunjuntak et al, *Lancet*, 338:1055–1059 (1991)). The incidence rates revealed were much higher than predicted, based on unsystematic surveillance. Systematic surveys have also demonstrated a surprising frequency of clinically mild yet, bacteremic typhoid infection among infants and toddlers in endemic areas (Ferreccio et al, *J. Pediatr.*, 104:899–901 (1984)).

Besides school age children in less-developed countries, two other populations at increased risk of typhoid fever are travelers and clinical microbiologists. Among U.S. travelers, the risk is highest in countries along the Pacific coast of South America, and in the Indian sub-continent (Ryan et al, *Rev. Infect. Dis.,* 11:1–8 (1989); and Mathieu et al, *Arch. Intern. Med.,* 154:1713–1718 (1994)). In addition, clinical microbiologists, including those in industrialized countries, have increased exposure to *Salmonella typhi* in the work environment, and therefore constitute a high risk group (Blaser et al, *J. Clin. Microbiol.,* 13:855–858 (1981)).

III. Multi-Resistant *S. typhi* Strains

Since, circa 1990, sporadic cases and localized outbreaks of typhoid fever have begun to appear in the Middle East, Northeast Africa and South and Southeast Asia. These outbreaks are caused by strains of *S. typhi* encoding plasmid-mediated resistance to trimethoprim/sulfamethoxazole, as well as resistance to chloramphenicol (Gupta et al, *Pediatr. Infect. Dis.,* 13:124–140 (1994); and Rowe et al, *Lancet,* 336:1065–1066 (1990)). Therapy against such strains requires the use of quinolone antibiotics, such as oral ciprofloxacin, or third generation cephalosporins, such as parenteral ceftriaxone. These antibiotics are costly for developing countries. In contrast with previous antibiotic-resistant strains that caused sporadic cases or extended epidemics, as in Mexico from 1972–1973 (Olarte et al, *Antimicrob. Agents Chemother.,* 4:597–601 (1973)); and in Peru from 1979–1981 (Goldstein et al, *J. Infect. Dis.,* 2:261–266 (1986)), and that eventually disappeared to be replaced once again by sensitive strains, the multiple antibiotic-resistant *S. typhi* strains that appeared in the Middle East and the Indian sub-continent circa 1990 are still the dominant strains in those areas. Moreover, these multiple antibiotic-resistant strains have spread widely, and are prevalent in Northeast Africa (Mikhail et al, *Trans. R. Soc. Trop. Med. Hyg.,* 83:120(1989)), and Southeast Asia (Vinh et al, *Antimicrob. Agents Chemother.,* 40:958–961(1996)).

It appears that *S. typhi* manifesting resistance to multiple previously useful antibiotics may be here to stay. Thus, typhoid fever is no longer a disease that can be simply and inexpensively treated with oral antibiotics. Moreover, health authorities can no longer base typhoid control programs on early treatment of disease. Complications of typhoid fever and deaths are on the increase because of inappropriate, delayed or inadequate antibiotic therapy (Singh, *Indian Pediatr.,* 28:329–332(1991); Bhutta, *Ann. Trop. Paediatr.,* 16:299–306 (1996); and Gupta, supra).

Hence, the dissemination of these multiple antibiotic-resistant *S. typhi* strains constitutes an increasing public health crisis in many less-developed countries, and has re-kindled interest in the development of improved oral typhoid vaccines. Immunoprophylaxis should also be considered for children in high incidence areas, particularly where *S. typhi* strains are multiple antibiotic-resistant, as well as for travelers and for clinical microbiologists.

IV. Early Vaccines Against Typhoid Fever

A. Inactivated Parenteral Whole-Cell Vaccines

The heat-inactivated, phenol-preserved whole-cell vaccine developed at the end of the 19th century (Wright et al, *Br. Med. J.,* 1:256–258 (1897); and Pfeiffer et al, *Dtsch. Med. Wochescr.* 22:735–737 (1896)) was shown, in randomized, controlled field trials sponsored by the World Health Organization in the 1960s, to confer moderate levels of protection (51–67% vaccine efficacy) that endured for up to seven years (Ashcroft et al, *Am. J. Hyg.,* 79:196–206 (1964); Ashcroft et al, *Lancet,* 2:1056–1060 (1967); Yugoslav Typhoid Commission, *Bull. WHO,* 30:623–630 (1964); and Hejfec, *Bull. WHO,* 34:321–339 (1966)). However, this is a distinctly unsatisfactory vaccine because it causes adverse reactions at an unacceptably high frequency, and therefore, has never become a popular public health tool (Levine, *Typhoid Fever Vaccines, In: Vaccines,* 2nd Ed., Ed. Plotkin et al, Philadelphia, Pa., W. B. Saunders (1994)). In controlled trials, approximately 25% of recipients of the heat-inactivated phenol-preserved whole-cell vaccine develop fever and systemic reactions, and about 15% tend to be absent from work or school after vaccination (Ashcroft et al (1964), supra; Yugoslav Typhoid Commission (1964), supra; and Hejfec, supra). For this reason, this vaccine has largely been replaced by two more recently licensed vaccines, live oral vaccine strain Ty21a (Vivotif$^R$), and the parenteral purified Vi capsular polysaccharide vaccine (TyphiViM$^R$) (Levine et al (1989a), supra). These two newer vaccines confer protection comparable to the above-noted whole-cell vaccine, but are very well-tolerated.

B. Parenteral Vi Polysaccharide Vaccine

As discussed above, in the mid 1930s, the Vi antigen, a polysaccharide capsule on *S. typhi,* was discovered (Felix et al (1934), supra). It was also shown that this antigen is present in the great majority of strains isolated from the blood of typhoid fever patients is a virulence factor of *S. typhi* in mice; its presence protects the O antigen from agglutination by O antiserum (Felix et al, *J. Hyg. Cambridge,* 49:92–109 (1951); and Felix et al, *J. Hyg.,* 35:421–427 (1935)). It was proposed that Vi antibody played an important role in protection against typhoid fever, and it was suggested that the phenol-inactivated whole-cell parenteral typhoid vaccine be replaced with alcohol-inactivated whole-cell parenteral vaccines. The rationale of this proposal was that the latter preserved Vi antigen better, and gave higher Vi antibody titers in animals and in humans (Felix, *BMJ,* 1:391–395 (1941)). However, in a randomized, controlled field trial in Yugoslavia, the heat and phenol-inactivated whole-cell parenteral vaccine was significantly more protective than an alcohol-inactivated vaccine (Yugoslav Typhoid Commission, *Bull. WHO,* 26:357–369 (1962)). Nonetheless, using the same rationale, an acetone-inactivated whole-cell parenteral typhoid vaccine has been proposed (Landy et al, *Am. J. Public Health,* 44:1572–1579 (1954)). In two independent field trials performed in the 1960s in Guyana and Yugoslavia, the acetone-inactivated vaccine conferred superior protection than the heat and phenol inactivated vaccine (Yugoslav Typhoid Commission (1962), supra). It has been argued that the superiority of the acetone-inactivated vaccine was due to better preservation of the Vi antigen (Wong et al, *J. Infect. Dis.,* 125:360–366 (1972)), or to higher antibody titers against the H antigen obtained with that vaccine.

A crucial advance was made by purifying the Vi antigen by a nondenaturing technique (Levine et al, *Infect. Immun.,* 12:1290–1294 (1975); and Robbins et al, *J. Infect. Dis.,* 150:436–449 (1984)) . The immunogenicity of two nondenatured Vi antigen lots prepared at the National Institutes of Health (Bethesda, Md.) and at the Institut Merieux, (Lyon, France) were evaluated (Tacket, *Vaccine,* 6:307–308 (1988)). Both lots elicited high titers of Vi antibody in about 90% of recipients. Moreover, it was shown that the Vi antibodies generated by the vaccines persisted for at least three years (Tacket et al (1988), supra). Levels of Vi antibody equal to those elicited by the parenteral purified Vi vaccine are seen in nature only in chronic typhoid carriers. In contrast, most patients convalescent from typhoid fever do not develop high titers of Vi antibody (Lanata et al, *Lancet,* 2:441–443 (1983); and Losonsky et al, *J. Clin. Microbiol.,* 25:2266–2269 (1987)).

Two randomized, controlled field trials were performed to assess the safety and efficacy of the candidate Vi antigen vaccine produced at the Institut Merieux. In both trials, the vaccine was well-tolerated (Acharya et al, supra; and Klugman et al, supra). In Nepal, a single 25 μg intramuscular dose of the Vi antigen vaccine provided 72% protection for at least 17 months against culture-confirmed typhoid fever in a study involving both children and adults (Klugman et al, supra). Similar results were obtained in a field trial in South African school children in whom the same dose of Vi antigen conferred 64% protection against culture-confirmed typhoid fever for at least 21 months (Klugman et al, supra).

Beyond its safety and efficacy in school children and in adults, an advantage of the Vi antigen vaccine is that it provides a moderate level of protection with just a single dose. However, compared to the attenuated typhoid vaccine Ty21a, a Vi antigen vaccine is disadvantageous in that it must be parenterally (intramuscularly) administered.

C. Early Attenuated Strains as Live Oral Vaccines

1. Streptomycin-Dependent *S. typhi* Vaccine Strains

The first attenuated strains to show promise as live oral typhoid vaccines were the streptomycin-dependent strains (SmD) developed in the late 1960s and early 1970s (DuPont et al, *Antimicrob. Agents Chemother.*, 10:236–239 (1970); and Levine et al, *J. Infect. Dis.*, 133:424–429 (1976)). When delivered in multiple spaced doses containing about $10^{10}$ colony forming units (cfu) per dose, the SmD strains were well-tolerated, and demonstrated approximately 80% protection against experimental challenge in a volunteer model of typhoid fever (DuPont et al, supra). However, when volunteers were immunized with lyophilized preparations that were re-constituted to make liquid suspensions of vaccine organisms, protection was not conferred (Levine et al (1976), supra). Because of this, further studies with the SmD vaccine strains were discontinued.

2. Strain Ty21a, a Licensed Live Oral Typhoid Vaccine

Ty21a, an attenuated strain of *S. typhi* that is safe and protective as a live oral vaccine, was developed in the early 1970s by chemical mutagenesis of pathogenic *S. typhi* strain Ty2 (Germanier et al, *J. Infect. Dis.*, 141:553–558 (1975)). The characteristic mutations in this vaccine strain that were initially presumed to be responsible for its attenuation include an inactivation of galE (which encodes UDP-galactose-4-epimerase, an enzyme involved in synthesis of lipopolysaccharide), and an inability to express Vi polysaccharide. Whereas Ty21a has proven to be remarkably well-tolerated in placebo-controlled clinical trials (Gilman et al, *J. Infect. Dis.*, 136:717–723 (1977); Wahdan et al (1982), supra; and Wahdan et al, *Bull. WHO*, 58:469–474 (1980)), it is not clear precisely what mutations are responsible for the stable, highly attenuated phenotype of this vaccine. Results of three double-blind, placebo-controlled studies that utilized active surveillance methods to assess the reactogenicity of Ty21a in adults and children showed that adverse reactions were not observed significantly more often in the vaccine recipients than the placebo group for any symptom or sign. Similarly, in large-scale efficacy field trials involving approximately 530,000 school children in Chile, 32,000 school children in Egypt, and approximately 20,000 pediatric and adult subjects in Indonesia, passive surveillance failed to identify vaccine-attributable adverse reactions (Ferreccio et al (1984), supra; Levine et al (1987a), supra; Simunjuntak et al, supra; Wahdan et al (1982), supra; and Wahdan et al (1980), supra).

Controlled field trials of Ty21a emphasize that the formulation of the vaccine, the number of doses administered, and the spacing of the doses, markedly influence the level of protection that can be achieved (Black et al, supra; Ferreccio et al (1984), supra; Levine et al (1987a), supra; and Wahdan et al (1980), supra). In the first randomized, placebo-controlled field trial of Ty21a in Alexandria, Egypt, 6–7 year old school children received three doses of lyophilized vaccine that was re-suspended in a diluent (every other day interval between the doses) (Wahdan et al (1980), supra). To neutralize gastric acid, the children chewed a 1.0 g tablet of $NaHCO_3$ several minutes before ingesting the vaccine or placebo. During three years of surveillance, Ty21a was shown to confer 96% protective efficacy against confirmed typhoid fever (Wahdan et al (1982), supra).

A more recent formulation that has constituted the commercial product since the mid-1980s consists of lyophilized vaccine in enteric-coated, acid-resistant, capsules. In a randomized, placebo-controlled field trial in Santiago, Chile, three doses of this enteric-coated formulation given within one week provided 67% efficacy during the first three years of follow-up (Levine et al (1987a), supra), and 63% protection over seven years of follow-up. Four doses of Ty21a in enteric-coated capsules given within eight days are significantly more protective than two or three doses (Ferreccio et al (1984), supra). When Ty21a was licensed by the U.S. Food and Drug Administration in late 1989, the recommended schedule was four doses to be given every other day; other countries use a three-dose immunization schedule.

However, recognized drawbacks of Ty21a include the lack of a molecular basis for its attenuation, its modest immunogenicity and, most importantly, the need to administer at least three spaced doses in order to confer protection. Another drawback of Ty21a is that it does not stimulate serum IgG anti-Vi antibody.

3. Correlations of Protection After Immunization with Attenuated Vaccines

Although licensed live oral typhoid vaccine strain Ty21a is only modestly immunogenic, and requires three or four spaced doses to elicit protection, the efficacy is surprisingly long-lasting, enduring for 5–7 years. The results of two immunological assays were found to correlate with the protection conferred by different formulations and immunization schedules of Ty21a in field trials. These include serum IgG O antibody seroconversions (Levine et al, *Rev. Infect. Dis.*, 11(suppl 3):S552–S567 (1989b)), and enumeration of gut-derived IgA O antibody secreting cells (ASCs) detected among peripheral blood mononuclear cells (PBMCs) (Kantele, *Vaccine*, 8:321–326 (1990); Tacket et al, *Infect. Immun.*, 60:536–541 (1992b); and Van de Verg et al, *Infect. Immun.*, 58:2002–2004 (1990)). The identification of these measurements as immunological correlates of protection provides an invaluable tool for use in early clinical trials when evaluating new attenuated *S. typhi* strains as possible live oral vaccines.

V. New Generations of Attenuated *S. typhi* As Live Oral Vaccines

Investigators in various laboratories worldwide have undertaken the task of engineering new candidate vaccine strains that will be as well-tolerated as Ty21a but, considerably more immunogenic such that a single oral dose will elicit protective immunity. Towards that end, candidate vaccine strains have been prepared by inactivating genes encoding various biochemical pathways, global regulatory systems, heat shock proteins, other regulatory genes, and putative virulence properties (Curtiss et al, *Infect. Immun.*, 55:3035–3043 (1987), supra; Edwards et al, *J. Bacteriol.*, 170:3991–3995 (1984); Hohmann et al, *J. Infect. Dis.*, 173:1408–1414 (1996a); Hone et al, *Infect. Immun.*, 56:1326–1333 (1988); Hone et al, *Vaccine*, 9:810–816 (1991); and Levine et al, *J. Biotechnol.*, 44:193–196 (1996)). One attempt has also been made to increase the immunogenicity of Ty21a by restoring its ability to express the Vi antigen (Cryz et al, *Infect. Immun.*, 57:3863–3868 (1989); and Tacket et al (1991), supra). The relative attenuating potential of these mutations has typically been assessed by feeding *S. typhimurium* strains harboring these mutations to mice, and comparing the result with that elicited by isogeneic wild-type strains. The mutations introduced into various recombinant *S. typhi* strains that were fed to humans as live oral vaccine candidates in clinical trials are summarized in Table 1 below.

TABLE 1

| Mutated Gene | Vaccine Strain | Wild-type Parent | Clinical Phenotype | Immunological Phenotype |
| --- | --- | --- | --- | --- |
| galE, via | EX462 | Ty2 | Not attenuated | Immunogenic |
| aroA, purA | 541Ty | CDC1080 | Overly attenuated | Poorly Immunogenic |
| aroA, purA, Vi | 543Ty | CDC1080 | Overly attenuated | Poorly Immunogenic |
| aroC, aroD | CVD 908 | Ty2 | Attenuated | Immunogenic |
| aroC, aroD, htrA | CVD 908-htrA | Ty2 | Attenuated | Immunogenic |
| cya, crp | X3927 | Ty2 | Insufficiently attenuated | Immunogenic |
| cya, crp, cdt | X4073 | Ty2 | Attenuated | Immunogenic |
| phoP/phoQ | Ty800 | Ty2 | Attenuated | Immunogenic |

The salient features and results of clinical trials with the most important attenuated strains of *S. typhi* that have played a pivotal role in live oral typhoid vaccine development are summarized below.

A. Vi+ Ty21a Strain

A derivative of Ty21a was constructed by introducing viaB (encoding the structural genes required for synthesis of Vi polysaccharide) from wild-type strain Ty2 into the chromosome of Ty21a, and demonstrating expression of Vi capsular polysaccharide (Cryz et al, supra). The resulting Vi+ Ty21a strain was fed to healthy North American adults in single doses of liquid suspensions containing $5.0 \times 10^5$, $5.0 \times 10^7$ and $5.0 \times 10^9$ cfu and buffer; an additional group of subjects received three $5.0 \times 10^9$ cfu doses and buffer (every other day interval between the doses) (Tacket et al (1991), supra). The Vi+ Ty21a strain was well-tolerated, and most subjects who received three doses developed rises in serum IgG antibodies and IgA ASCs against *S. typhi* O antigen. However, no subject manifested rises in serum IgG anti-Vi antibody, or exhibited ASCs that secrete IgA anti-Vi antibody (Tacket et al (1991), supra).

B. EX462

An attempt was made to construct a new derivative of Ty2 using recombinant DNA techniques that would contain, what were thought at the time to be, the attenuating mutations in Ty21a that had been induced by chemical mutagenesis (Hone et al (1988), supra). Specifically, the derivative harbored a deletion mutation in galE, and was incapable of expressing Vi polysaccharide, but did not have the multiple other mutations present in Ty21a as a result of its being obtained using non-specific chemical mutagenesis. The resultant strain, EX462, was clearly insufficiently attenuated, as it caused a typhoid fever-like syndrome in several recipients. These observations demonstrate conclusively that the combination of the galE mutation and inability to express Vi antigen by themselves are not responsible for the attenuation of strain Ty21a.

C. Strains 541Ty and 543Ty

The concept of making auxotrophic mutants of Salmonella with inactivation of genes encoding enzymes in the aromatic amino acid biosynthesis pathway has been popularized (Edwards et al, supra; and Hoiseth et al, *Nature*, 292:238–239 (1981)). These mutations render the Salmonella nutritionally dependent on substrates (para-aminobenzoic acid and 2,3-dihydroxybenzoate) that are not available in sufficient quantity in mammalian tissues; as a consequence, the vaccine remains viable but, is severely inhibited in its ability to proliferate.

Prototype aroA− strains 541Ty and 543Ty (a Vi− variant of 541Ty) were constructed from CDC1080, a wild-type strain obtained from the Centers for Disease Control (Edwards et al, supra). The pathogenicity of strain CDC1080 has never been directly tested in volunteers. In contrast, most other investigators have started with wild-type strain Ty2, the parent of Ty21a (Germanier et al, supra), in their attempts to engineer new attenuated strains. The pathogenicity of Ty2 has been established in volunteer studies (Hornick et al, *N. Engl. J. Med.*, 283:686–691 and 739–746 (1970)).

Strains 541Ty and 543Ty also harbor a deletion mutation in purA, which results in a specific requirement for adenine (or an assimilable compound, such as adenosine) (Edwards et al, supra). A third mutation in hisG, leading to a histidine requirement, does not affect virulence but, provides an additional biochemical marker to clearly differentiate the vaccine strain from wild-type *S. typhi*.

Strains 541Ty and 543Ty were quite well-tolerated in dosages up to $5.0 \times 10^{10}$ cfu in Phase 1 studies but, were notably less immunogenic than Ty21a in stimulating humoral antibody responses (Levine et al, *J. Clin. Invest.*, 79:888–902 (1987b)). For example, only 11% of subjects developed serum IgG anti-O antibodies (Levine et al (1987b), supra).

D. Strain CVD 908

One vaccine strain that has proven to be well-tolerated and highly immunogenic following administration of a single oral dose in Phase 1 clinical trials in humans with freshly-harvested organisms is strain CVD 908 (Tacket et al (1992b), supra; and Tacket et al (1992a), supra) , which harbors precise deletion mutations in aroC and aroD (Hone et al (1991), supra). Indeed, CVD 908 was the first genetically-engineered *S. typhi* vaccine candidate shown to be highly immunogenic yet, well-tolerated, thereby generating optimism that it might be possible to develop a single-dose live oral typhoid vaccine. At a well-tolerated dose of $5.0 \times 10^7$ cfu, 92% of CVD 908 recipients manifested IgG O antibody seroconversions, and showed evidence of priming of the intestinal immune system (IgA ASCs) (Tacket et al (1992a), supra).

1. Cell-Mediated Immune Response After Immunization with Attenuated Vaccine CVD 908

The clinical trials with CVD 908 have been characterized by intensive investigations of cell-mediated immune (CMI) responses (Sztein et al, *J. Immunol.*, 155:3987–3993 (1995); and Sztein et al, *J. Infect. Dis.*, 170:1508–1517 (1994)). When administered to healthy adults, CVD 908 triggers CMI responses to *S. typhi* antigens, including cytokine production, and proliferative responses to heat and phenol-inactivated whole-cell *S. typhi* particles and purified flagella (Sztein et al (1994), supra).

Since *S. typhi* are intracellular pathogens, it has also been surmised that cytotoxic lymphocyte (CTL) responses might play an important role in limiting the progression of typhoid infection by destroying host cells harboring *S. typhi*. Thus, a CTL assay was developed to evaluate whether immunization of adult volunteers with attenuated S. typhi CVD 908 elicits CTL effectors in blood capable of killing Epstein-Barr virus (EBV)-transformed autologous B lymphocytes infected with wild-type S. typhi (Sztein et al (1995), supra). CTL activity was evaluated by using PBMC isolated before and at 14 and 29 days after the first immunization. PBMC were either used immediately in CTL assays or expanded in vitro for 6–8 days in the presence of S. typhi-infected autologous EBV-transformed cells prior to the measurement of CTL responses. Using this system, CTL effectors lysed S. typhi-infected autologous EBV-transformed cells. The specific CTL activity was observed in PBMC preparations obtained 14 days after immunization, and following 7 to 8 days of in vitro expansion in the presence of S. typhi-infected autologous EBV-transformed cells. PBMC obtained 29 days after immunization exhibited comparable or greater CTL activity levels than those observed in cells isolated 14 days after immunization. The CTL effector cell population in these PBMC cultures was a classic $CD8^+$, MHC class I-restricted, cytotoxic T lymphocyte population (Sztein et al (1995), supra). The observation that immunization with attenuated S. typhi elicits circulating $CD8^+$, MHC class I-restricted, CTL effector cells capable of killing autologous S. typhi-infected targets supports the contention that CTL play a crucial role in limiting the progression of typhoid infection by destroying host cells harboring bacteria.

2. Disadvantages of Attenuated Vaccine Strain CVD 908

A possible drawback observed in the Phase 1 clinical trials with CVD 908 is that 50% of subjects who ingested this vaccine strain at a dose of $5.0 \times 10^7$ cfu, and 100% of subjects who received a dose of $5.0 \times 10^8$ cfu, manifested silent vaccinemias, wherein vaccine organisms were recovered from blood cultures collected at one or more time points between day 4 and day 8 after vaccination. The blood cultures were collected systematically in these individuals within hours after they ingested vaccine, and then on days 2, 4, 5, 7, 8, 10, 14, 20, 27 and 60. No blood cultures from any vaccinee were positive prior to day 4 nor after day 8. The vaccinemias appeared to have no clinical consequence (e.g., they were not associated with fever), and they were short-lived, spontaneously disappearing without the use of antibiotics. However, the possible consequences that vaccinemia with an attenuated S. typhi strain may have in a large population where immunocompromised individuals are likely to be included is unknown. Another perceived disadvantage of CVD 908 is the production of fever in a small proportion of vaccinees who receive a high dose of vaccine (Tacket et al (1992a), supra).

As an alternative, additional mutations were sought to be introduced into CVD 908 to yield a derivative that remains well-tolerated and immunogenic yet, would not manifest vaccinemias or fever.

E. CVD 908-htrA

It was found that inactivation of htrA, a gene encoding a stress protein that also functions as a serine protease, attenuates wild-type S. typhimurium in a mouse model (Chatfield et al, Microbial. Pathogenesis, 12:145–151 (1992a)). Moreover, mice immunized orally with S. typhimurium harboring a deletion mutation in htrA were protected against subsequent challenge with a lethal dose of wild-type S. typhimurium (Chatfield et al (1992a), supra). Therefore, a deletion mutation was introduced into htrA of CVD 908, resulting in strain CVD 908-htrA (Levine et al (1996), supra). A single dose of CVD908-htrA was fed to three groups of subjects who ingested $5.0 \times 10^7$ (N=7), $5.0 \times 10^8$ (N=8) or $5.0 \times 10^9$ (N=7) cfu (Tacket et al (1997), supra). The CVD 908-htrA strain was as well-tolerated as the CVD 908 parent. Only one of these 22 subjects developed a low-grade fever, which was detected by routine surveillance, and was not associated with any complaints of malaise. However, 2 of the 22 subjects developed loose stools (Tacket et al (1997), supra). Similarly, the immune response was excellent: 20 of 22 individuals (91%) manifested significant rises in serum IgG O antibody, and gut-derived IgA ASCs that made antibody to O antigen were detected in 100% of the vaccinees. These immunologic responses are virtually identical to those observed in Phase 1 clinical trials in subjects immunized with comparable doses of CVD 908 (Tacket et al (1992a), supra). The one striking difference was with respect to vaccinemias. Whereas vaccinemias were detected in 12 of 18 subjects who received a $5.0 \times 10^7$ or $5.0 \times 10^8$ cfu dose of CVD 908, no vaccinemias were detected in any of the 22 individuals who ingested well-tolerated, highly immunogenic $5.0 \times 10^{7-9}$ cfu doses of CVD 908-htrA (p<0.001) (Levine et al (1987b), supra; Tacket et al (1992a), supra; and Tacket et al (1997), supra). CVD 908-htrA also elicits strong cell-mediated immune responses in vaccinees comparable in strength to those recorded with CVD 908 (Tacket et al (1992a), supra; and Tacket et al (1997), supra). Based on these highly encouraging data, CVD 908-htrA has entered Phase 2 clinical trials to assess its clinical acceptability and immunogenicity in larger numbers of subjects, including children.

F. Strains with Mutations in cya, crp or cya, crp, cdt

In Salmonella, the genes cya (encoding adenylate cyclase) and crp (cyclic AMP receptor protein) constitute a global regulatory system that affects many genes and operons (Curtiss et al, Dev. Biol. Stand., 82:23–33 (1994)). S. typhimurium that harbor deletions in cya and crp are attenuated compared to their wild-type parent, and oral immunization protects mice against challenge with virulent S. typhimurium (Curtiss et al (1987), supra).

Vaccine candidate strain $\chi 3927$, a $cya^-$, $crp^-$ double mutant of S. typhi strain Ty2 was constructed (Curtiss et al (1994), supra). In Phase 1 clinical trials, it was demonstrated that strain $\chi 3927$ was attenuated compared to the wild-type strain but, insufficiently attenuated to serve as a live oral vaccine in humans, as occasionally subjects developed high fever and typhoid-like symptoms (Tacket et al (1992b), supra). Several subjects also manifested vaccinemias (Tacket et al (1992b), supra).

In order to achieve a greater degree of attenuation, a third deletion mutation in cdt was introduced into the $cya^-$, $crp^-$ mutant $\chi 3927$ (Curtiss et al (1994), supra). cdt is a gene that affects the dissemination of Salmonella from gut-associated lymphoid tissue to deeper organs of the reticuloendothelial system, such as the liver, spleen and bone marrow (Kelly et al, Infect. Immun., 60:4881–4890 (1992)). The resultant $cya^-$, $crp^-$, $cdt^-$ triple mutant strain, $\chi 4073$, was fed to healthy adult North Americans, with buffer, in single doses containing $5.0 \times 10^5$, $5.0 \times 10^6$, $5.0 \times 10^7$ or $5.0 \times 10^8$ cfu (Tacket et al (1997), supra). The strain was well-tolerated, except for one individual in the $5.0 \times 10^7$ cfu group who developed diarrhea (Tacket et al (1997), supra). No subjects manifested vaccinemia. Four of five subjects who ingested $5.0 \times 10^8$ cfu exhibited significant rises in serum IgG O antibody, and had ASCs that made IgA O antibody (Tacket et al (1997), supra).

G. Strains with Mutations in phoP/phoQ

Two candidate S. typhi strains harboring deletions in phoP/phoQ have been constructed (Hohmann et al (1996a), supra; and Hohmann et al, Vaccine, 14:19–24 (1996b)). Strain Ty445, which also harbors a deletion in aroA, was found to be overly attenuated and only minimally immunogenic (Hohmann et al (1996b), supra). In contrast, strain Ty800, a derivative of Ty2 having deletions in only phoP, phoQ was generally well-tolerated and immunogenic when evaluated in dosage levels from $10^7$ to $10^{10}$ cfu in a small Phase 1 clinical trial involving 11 subjects (Hohmann et al (1996b), supra). At the highest dosage level, 1 of 3 vaccinees developed diarrhea (10 loose stools) . It is difficult to compare the immune responses of subjects who received Ty800 with those observed in recipients of CVD 908-htrA and χ4073, since some of the immunological assay techniques were different, and even where the same assay was used (e.g., IgA ASCs that make O antibody), considerable variation is known to occur between laboratories.

H. Summary

CVD 908 is well-tolerated but, is associated with vaccinemias in approximately 50% of subjects who ingest a $10^7$ cfu dose. Mild, but definite diarrhea, has been observed in approximately 10% of subjects who have ingested CVD 908-htrA, Ty800 or χ4073. The immune response to χ4073 was less potent than that observed after oral immunization with CVD 908, CVD 908-htrA and, apparently, Ty800 (see Table 1 above). Thus, although there exist four attenuated *S. typhi* strains that have completed Phase 1 clinical trials, each is associated with at least one drawback of sufficient concern that there is interest in the development of additional candidate attenuated *S. typhi* vaccine strains. Moreover, none of these four strains has succeeded in eliciting serum IgG anti-Vi antibody, a known protective immune response.

VI. Use of Attenuated Salmonella Strains as Live Vector Vaccines to Express Foreign Genes Encoding Protective Antigens from Other Pathogens and Deliver those Antigens to the Immune System Live vector vaccines, also called "carrier vaccines" or "live antigen delivery systems", comprise an exciting and versatile area of vaccinology (Levine et al, *Microecol. Ther.*, 19:23–32 (1990); Morris et al, *Gastroenterol.*, 103:699–702 (1992); Barletta et al, *Res. Microbiol.*, 141:931–940 (1990); Dougan et al, *Para. Immunol.*, 9:151–160 (1987) ; and Curtiss et al, *Curr. Top. Microbiol. Immunol.*, 146:35–49 (1989)). In this approach, a live viral or bacterial vaccine is modified so that it expresses protective foreign antigens of another microorganism, and delivers those antigens to the immune system, thereby stimulating a protective immune response. Live bacterial vectors that are being promulgated include, among others, attenuated Salmonella (Levine et al (1990), supra; Morris et al, supra; Dougan et al, supra; and Curtiss et al (1989), supra), *Bacille Calmette Guerin* (Barletta et al, supra), *Yersinia enterocolitica* (Van Damme et al, *Gastroenterol.*, 103:520–531 (1992)), *V. cholerae* O1 (Viret et al, *Mol. Microbiol.*, 7:239–252 (1993)), and *E. coli* (Hale, *Res. Microbiol.*, 141:913–919 (1990)). Each has certain advantages and some disadvantages.

Attenuated *S. typhi* is particularly attractive as a live vector vaccine for humans because it is administered orally, colonizes the gut-associated lymphoid tissue as well as the reticuloendothelial system, elicits a broad immune response (that includes serum antibodies, mucosal SIgA, diverse cell-mediated immune responses including classical CTL, and a form of antibody-dependent cellular cytotoxicity) (Conry et al, *Gene Therapy*, 2:59–65 (1995); Cox et al, *J. Virol.*, 67:5664–5667 (1993); Davis et al, *Proc. Natl. Acad. Sci., USA*, 93:7213–7218 (1996a); Davis et al, *Vaccines*, 96:111–116, Brown et al, (Eds.), Cold Spring Harbor Laboratory Press (1996b); Tacket et al (1992a), supra; Gonzalez et al, *J. Infect. Dis.*, 169:927–931 (1994); and Sztein et al (1994), supra). Moreover, Salmonella are readily manipulated genetically, and many foreign antigens have already been expressed in these bacteria. In theory, one-dose oral vaccines against a variety of infectious diseases can be developed by stably introducing and expressing foreign genes encoding protective antigens in a well-tolerated yet, highly immunogenic *S. typhi* live vector strain (Levine et al (1990), supra)

VII. Salmonella with Mutations in the Purine Metabolic Pathway

A. Early Reports of Salmonella Strains with Mutations in the Purine Metabolic Pathway purA and purB mutations in Salmonella (interrupting the de novo biosynthesis of adenine nucleotides) (see FIG. 2) are so highly attenuating (McFarland et al, *Microb. Pathogen.*, 3:129–141 (1987)) that these strains are non-protective in animals (O'Callagham et al, *Infect. Immun.*, 56:419–423 (1988)), and are poorly immunogenic in humans (Levine et al (1987b), supra). In contrast, mutations in several of the genes involved in the common purine pathway (i.e., purF, purG, purC, purHD) that interrupt the biosynthesis of both purine nucleotides (see FIG. 2), or in guaB or guaA, thereby interrupting the biosynthesis of guanine nucleotides (see FIG. 2), have been reported to be far less attenuating (McFarland et al, supra); indeed, such strains induced death in mice in doses as low as $10^2$ cfu (McFarland et al, supra).

The observations reviewed above suggest that:

(i) mutations affecting enzymes of the common purine pathway are mildly attenuating (McFarland et al, supra); and (ii) mutations distal to the common pathway and affecting the synthesis of adenine nucleotides are over-attenuating (i.e., purA, purB) (McFarland et al, supra; O'Callagham et al, supra; and Levine et al, (1987b) supra), but distal mutations affecting the guanine nucleotide synthesis are only minimally attenuating (McFarland et al, supra).

B. Unexpected and Unique Observations in the Present Invention

Based on the published observations reported above, it was therefore unexpectedly discovered that a specific gua auxotrophy in *S. typhi* provided a high degree of attenuation. This attenuation is believed to be due, in part, to reduced invasiveness (a property that has not been previously described in other Salmonella spp. with attenuating mutations in metabolic pathways) as well as to the decreased intracellular replication rate of ΔguaB–A *S. typhi* mutants. This finding was unexpected since *S. dublin* and *S. typhimurium* harboring insertional Tn5 mutations affecting guanine nucleotide synthesis were reported to be only minimally attenuated (McFarland et al, supra). Furthermore, another unexpected finding was that despite this high degree of attenuation, ΔguaB–A *S. typhi* strain CVD 915 described herein was very immunogenic in a murine animal model. This observation is unexpected from previous reports in which highly attenuated strains, with mutations inactivating purA and purB, have been very poorly immunogenic (Edwards et al, supra). Also, another unexpected observation was that strain CVD 915 induced an impressive immune response to a recombinant antigen expressed in the same attenuated strain. This observation is unexpected from previously reported observations in which highly attenuated strains have been poor live vectors for recombinant heterologous antigens (Tacket et al (1997), supra).

Moreover, strain CVD 915 was able to deliver a eukaryotic expression vector encoding a recombinant foreign antigen (DNA-medicated vaccine) and elicit an astounding immune response. The property of delivering a eukaryotic expression vector plasmid has been reported with attenuated Shigella vectors (Sizemore et al, *Science*, 270:299–302

(1995)); and with attenuated *Salmonella typhimurium* vectors (Darji et al, *Cell*, 91:765–775 (1997)). Shigella spp. are invasive organisms and their success in delivering DNA vaccines is thought to be secondary to the fact that they leave the phagosome immediately after invasion (Sansonetti et al, *Infect. Immun.*, 51:461–469 (1986)). However, Salmonella does not leave the phagosome after invasion. Therefore, the observation presented herein is unexpected from the previous concept and is unique.

In summary, in the present invention a unique method has been devised to genetically-engineer attenuated Salmonella to achieve the constitutive and stable expression of the Vi antigen. Further, the Salmonella mutants of the present invention preferably are also attenuated by mutations in the de novo guanine metabolic pathway.

SUMMARY OF THE INVENTION

An object of the present invention is to provide attenuated strains of Salmonella that constitutively express the Vi antigen.

Another object of the present invention is to provide a method to achieve constitutive expression of the Vi antigen.

Still another object of the present invention is to provide Salmonella which are also attenuated by mutations in the de novo guanine metabolic pathway.

Yet another object of the present invention is to provide a method to achieve a deletion mutation in the guaB and guaA genes of Salmonella.

An additional object of the present invention is to provide an oral or intranasal (i.e., a mucosal) vaccine against typhoid fever.

A further object of the present invention is to provide Salmonella strains which are useful as live vectors of foreign genes cloned from other pathogens, and that upon expression and appropriate immunization, will raise protective immune responses against the pathogens from which the foreign antigens were derived.

A still further object of the present invention is to provide Salmonella strains which are useful as live vectors to deliver DNA-mediated vaccines.

These and other objects of the present invention, which will be apparent from the detailed description of the invention provided below, have been met, in one embodiment, by an attenuated Salmonella mutant, wherein said mutant constitutively expresses Vi antigen.

BRIEF DESCRIPTION OF THE DRAWINGS

In FIG. 2, interrupted arrows illustrate pathways in which the individual steps are not represented. Enzymes are represented by their genes. Superscript letters represent selected strains with a mutation of the gene involved in that reaction. The strains represented are: a: purF1741::Tn10 *S. dublin* SL5437 (McFarland et al, supra); b:purG876::Tn10 *S. dublin* SL5436 (McFarland et al, supra); c:purC882::Tn10 *S. dublin* SL5435 (McFarland et al, supra); d:purH887::Tn10 *S. dublin* SL2975 (McFarland et al, supra); e:ΔguaB–A *S. flexneri* 2a CVD 1204 and ΔguaB–A, ΔvirG *S. flexneri* 2a CVD 1205 (Noriega et al, *Infect. Immun.*, 64:3055–3061 (1996)) and ΔguaB–A *Salmonella typhi* CVD 915 (present invention); f:aroD25::Tn10 *S. flexneri* Y SFL114 (Lindberg et al, (1990) supra), SFL124 (Li et al, supra), *S. flexneri* 2a 1070 (Karnell et al (1995) supra); g:ΔaroC, ΔaroD *S. typhi* CVD 908 (Hone et al (1991), supra); h:hisG46 DEL407, aroA554::Tn10 *S. typhimurium* SL3261 (Hoiseth et al, supra) ; i:ΔaroA *S. flexneri* 2a CVD 1201 and ΔaroA, ΔvirG CVD 1203 (Noriega et al, *Infect. Immun.*, 62:5168–5172 (1995); and j:ΔaroA, ΔhisG, ΔpurA *S. typhi* 541Ty (Levine et al (1987b), supra). In FIG. 2, the abbreviations are defined as follows: PRPP:5-phosphoribosyl-β-1-pyrophosphate; PRA:5 - phosphoribosylamine; GAR:5'-phosphoribosyl-1-glycinamide; FGAR:5'-phosphoribosyl-N-formylglycinamide; FGAM:5'-phosphoribosyl-N-formylglycinamidine; AIR:5'-phosphoribosyl-5-aminoimidazole; CAIR:5'-phosphoribosyl-5-aminoimidazole-4-carboxylic acid; SAICAR:5'-phosphoribosyl-4-(N-succinocarboxamide)-5-aminoimidazole; AICAR:5'-phosphoribosyl-4-carboxamide-5-aminoimidazole; FAICAR:5'-phosphoribosyl-4-carboxamide-5-formamidoimidazole; IMP:inosinic acid; Hx:hypoxanthine; G:guanine; and A:adenine.

FIGS. 3A–3G show the DNA sequence encoding the guaA and guaB genes of *Escherichia coli* (SEQ ID NO: 1) (GenBank Accession Nos. M10101–M10102) (Thomas et al, *Gene*, 36:45–53 (1985); Tiedeman et al, *J. Biol. Chem.*, 260:8676–8679 (1985); and Tiedeman et al, *Nucleic Acids Res.*, 13:1303–1316 (1985)), which is considered to be highly homologous with the guaA and guaB of Salmonella spp., as well as some restriction endonuclease sites useful in creating the deletion mutants of the present invention.

DETAILED DESCRIPTION OF THE INVENTION

The present invention provides attenuated Salmonella for use, inter alia, as oral vaccines against typhoid fever, and as live vector and DNA-mediated vaccines expressing foreign antigens. As used herein, a "foreign antigen" means an antigen foreign to Salmonella.

Also, in the present invention, an attenuated Salmonella mutant is provided, wherein said mutant constitutively expresses the Vi antigen.

It is preferable in the present invention that the chromosomal genome of Salmonella is modified by substituting the highly regulated vipR promoter by a strong constitutive promoter, thus, making the expression of the Vi antigen in the attenuated Salmonella constitutive and stable. The particular constitutive promoter employed in the present invention is not critical thereto. Examples of such constitutive promoters include $P_{tac}$ (de Boer et al, Proc. Natl. Acad. Sci., 80:21–25 (1983)), $P_{lac}$ (De Boer et al, supra), $P_{trc}$ (De Sutter et al, Gene, 141:163–170 (1994)), $P_{Olac}$ and $P_{lpp}$ (De Sutter et al, supra; and Guisez et al, Protein Expr. Purif., 2:249–258 (1998)).

The particular S. typhi employed as a starting material in the present invention is not critical thereto.

In the examples herein the S. typhi vaccine was constructed from the wild-type S. typhi strain Ty2.

S. typhi Ty2 is a well-known virulent Salmonella strain available from a variety of sources, such as the CVD, the Centers for Disease Control (CDC), the Walter Reed Army Institute of Research, the Uniformed Services University of the Health Sciences, the Institut Pasteur (France), Imperial College (England).

Other wild-type S. typhi strains that have been used in the development of attenuated vaccine candidates, and which can be employed as starting materials in the present invention include: Strain CDC1080 (Levine et al (1987b), supra), which can be obtained from Stanford University or from the CDC, and strain ISP1820 (Hone et al (1991), supra), which can be obtained from the Center for Vaccine Development, University of Maryland.

Figure 2:
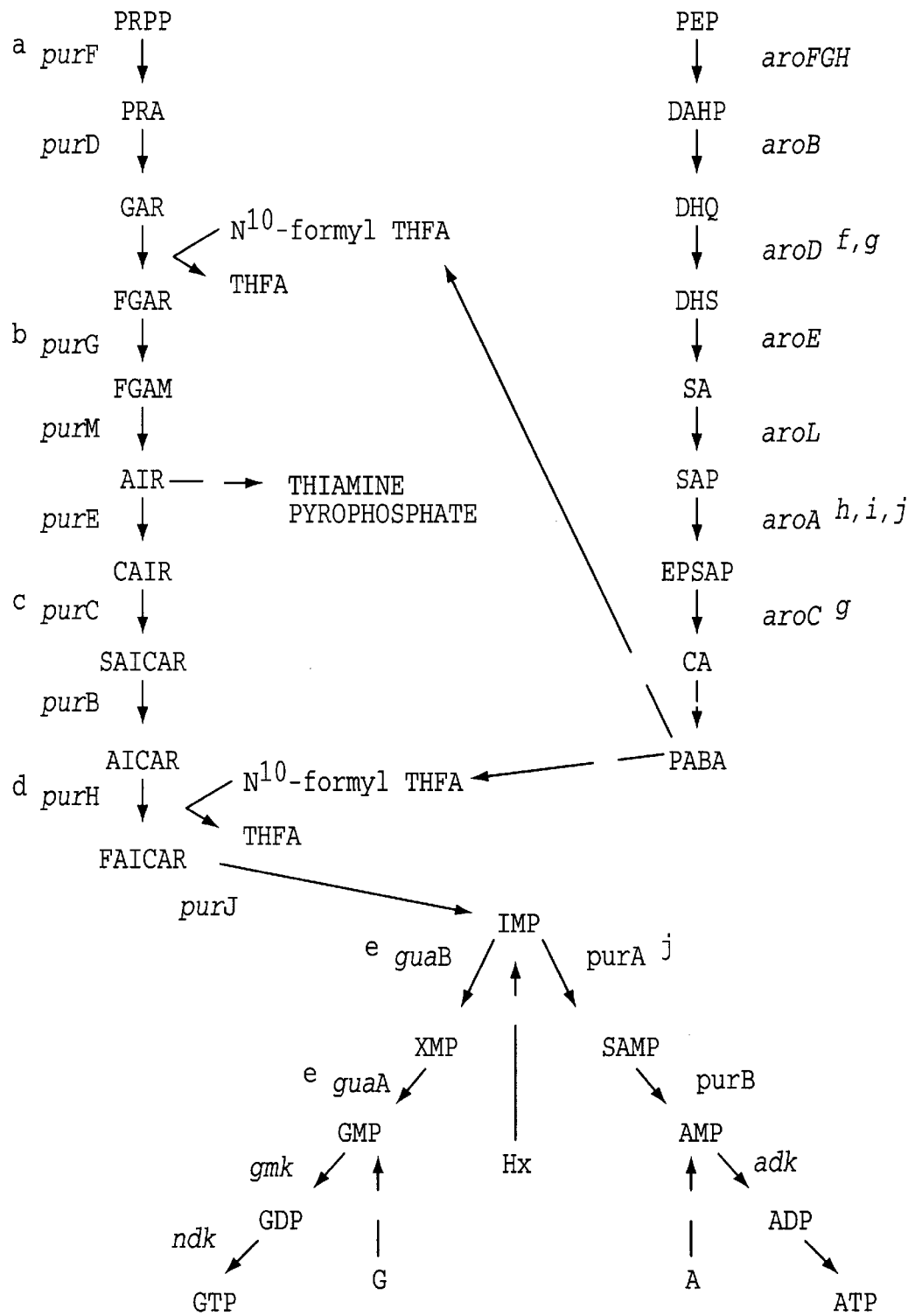
FIG. 2 shows the purine de novo biosynthesis pathway and contribution of the aromatic metabolic pathway.
Figure 4:
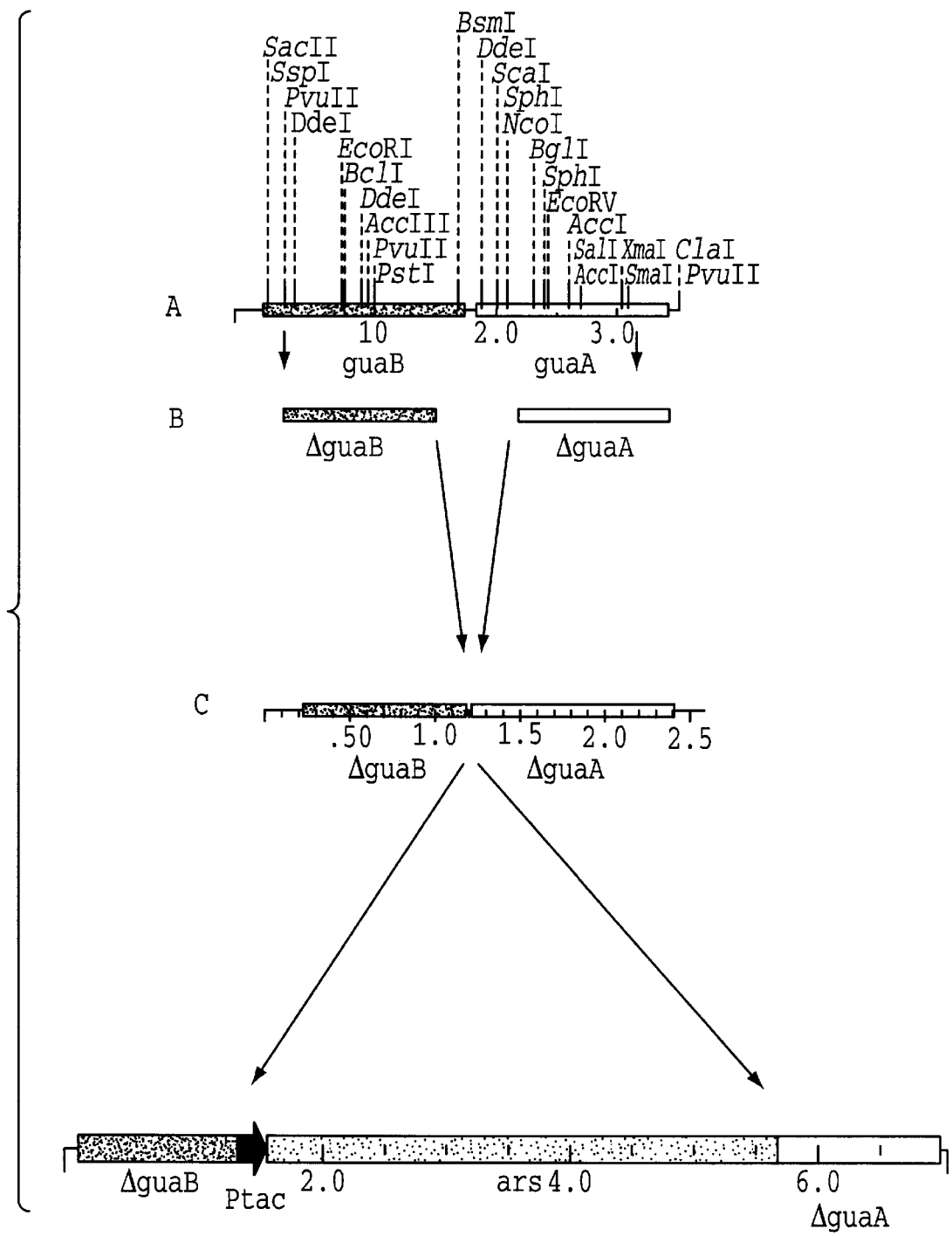
FIG. 4 schematically shows the orientation of the guaB–A operon, as well as the location of some restriction endonuclease sites useful in creating the deletion mutants of the present invention; the guaB–A operon segments amplified by PCR; and the fusion by PCR of the guaB–A operon segments constituting the ΔguaB–A allele. Also, shown is the cloning of the arsenite operon (ars) in the middle of the ΔguaB–A allele resulting in the ΔguaB–A::$P_{tac}$-ars cassette. This deletion cassette was subsequently cloned in a suicide plasmid and exchanged for the wild-type guaB–A allele in *S. typhi* strain Ty2, resulting in strain ΔguaB–A *S. typhi* CVD 915.
Figure 5:
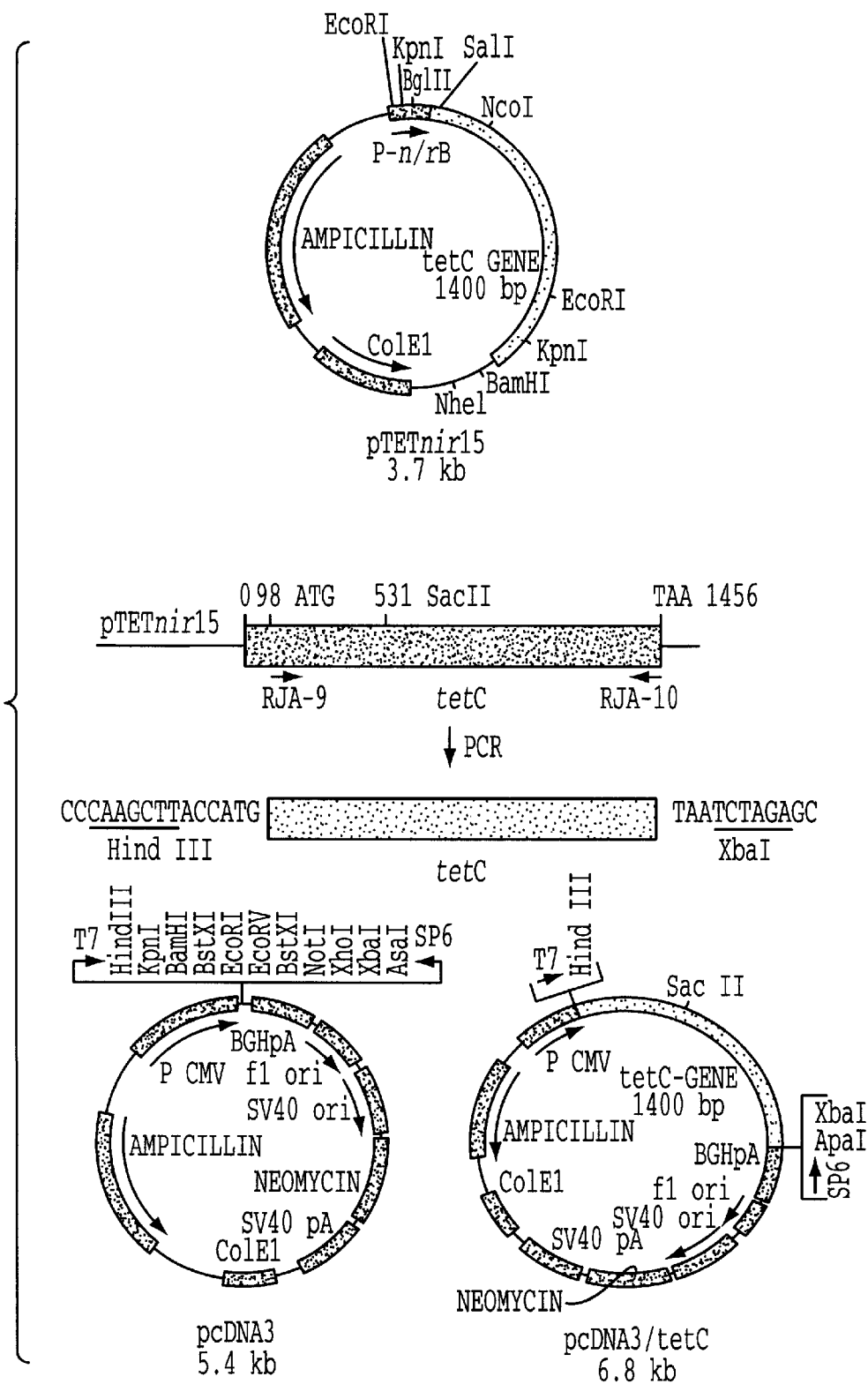
FIG. 5 is a schematic representation of the construction of pcDNA3/tetC (a DNA vaccine encoding tetanus toxin fragment C under the control of the human cytomegalovirus (CMV) promoter).
Figure 6:
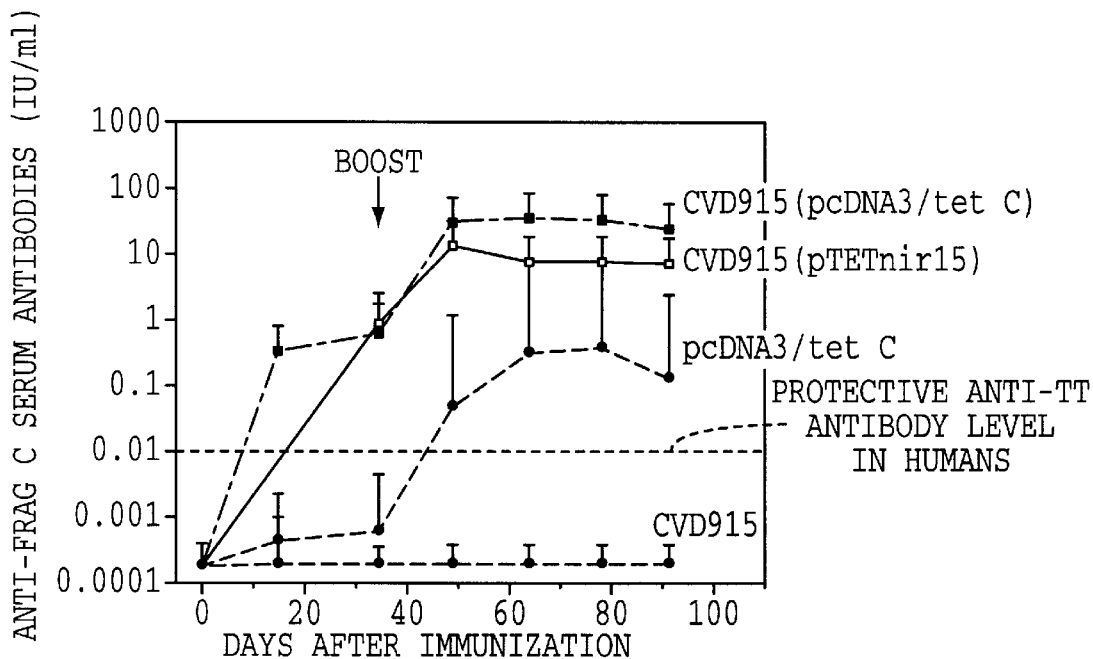
FIG. 6 shows the anti-fragment C antibody response in mice after intranasal immunization with strain ΔguaB–A CVD 915 expressing fragment C of tetanus toxin, or carrying an eukaryotic expression cassette encoding fragment C of tetanus toxin.

Preferably, in the present invention, the chromosomal genome of Salmonella is modified by removing or otherwise modifying the guaB–A operon, and thus blocking the de novo biosynthesis of guanine nucleotides. More preferably, a defined, in frame, non-polar mutation in the guaB–A operon inactivates the purine metabolic pathway enzymes IMP dehydrogenase (encoded by guaB) and GMP synthetase (encoded by guaA). As a consequence of these mutations, Salmonella are unable to de novo synthesize GMP, and consequently GDP and GTP nucleotides (see FIG. 2), which severely limits its grow in mammalian tissues. In vitro, the ΔguaB–A Salmonella mutants of the present invention are unable to grow in minimal medium unless supplemented with guanine. In tissue cultures, the ΔguaB–A Salmonella mutants of the present invention were found to show a significant reduction in their capability for invasion. ΔguaB–A Salmonella mutants may scavenge guanine nucleotides from the tissues of the mammalian host. However, their assimilation into Salmonella requires prior dephosphorylation to nucleosides by periplasmic nucleotidases to be incorporated as nucleotide precursors into the guanine salvage pathway. Therefore, as nucleotides are readily available in the intracellular environment of the mammalian host, the attenuation due to the de novo synthesis of guanine nucleotides is due either to the inefficiency of the salvage pathway or to reasons that are obscure to today's knowledge.

The guaA gene, which encodes GMP synthetase, is 1575 bp in size (see FIGS. 3A–3G). Thus, the size of an intracistronic inactivating deletion in the guaA mutant may range from 1 to 1575 bp, preferably, from 100 to 1575 bp if the deletion is in-frame. Deletions can also be made that extend beyond the guaA gene, i.e., extracistronic deletions downstream of the guaA may affect the transcription of this gene, and therefore inactivate it. However, the latter is not preferable.

The guaB gene, which encodes IMP dehydrogenase, is 1533 bp in size (see FIGS. 3A–3G). Thus, the size of an intracistronic deletion in the guaB mutant may range from 1 bp to 1533 bp, preferably, from 100 to 1533 bp if the deletion is in-frame. Deletions can also be made that extend beyond the guaB gene, i.e., extracistronic deletions downstream of the guaB may affect the transcription of both genes (guaB and guaA), and therefore inactivate it. However, the latter is not preferable.

Deletions can be made in the guaA gene using 2 convenient restriction sites located in the guaA gene; examples of these are ScaI or AccI and EcoRV or SalI or SmaI or SphI or XmaI (FIGS. 3A–3G and FIG. 4), or by site-directed mutagenesis with oligonucleotides (Sambrook et al, In: Molecular Cloning, A Laboratory Manual, Eds., Cold Spring Harbor Publications (1989)).

Deletions can be made in the guaB gene using two convenient restriction sites located in the guaB gene; examples of these are BclI and BsmI or EcoRI or PvuII or SacII or SspI or XhoII (FIGS. 3A–3G and FIG. 4), or by site-directed mutagenesis with oligonucleotides (Sambrook et al, supra).

In addition, any combination of restriction sites located simultaneously in the guaB and guaA genes can be used to obtain the deletion mutants of the present invention; examples of which include AccIII, AflIII, AhaII, AlwI, AlwNI, AsuI, BanI, BcnI, Bsp1286, BspMII, and DdeI (FIGS. 3A–3G).

Inactivation of the guaA gene and/or guaB gene can also be carried out by an insertion of foreign DNA using any of the above-mentioned restriction sites, or by site-directed mutagenesis with oligonucleotides (Sambrook et al, supra) so as to interrupt the correct transcription of guaB and/or guaA. The typical size of an insertion that can inactivate the guaA gene and guaB gene is from 1 base pair to 100 kbp, although insertions smaller than 100 kbp are preferable. The insertion can be made anywhere inside the guaA gene or guaB gene coding region or between the coding region and the promoter.

Other methods for the guaA gene and/or guaB gene inactivation include the transfer into Salmonella of deletions or insertions made in other enterobacteriae guaA or guaB genes, transposon-generated deletions, and imprecise excision of DNA insertions. The latter two methods are more likely to make deletions that extend beyond the guaA or guaB gene, and therefore are not preferable.

The gua mutants of the present invention are useful for the development of a non-reactogenic Salmonella candidate live oral vaccine.

Salmonella vaccine candidates can be constructed which, e.g., in addition to containing other attenuating mutations, fail to express the aro gene products. This can be accomplished by deleting the portion of at least one of the aro genes (aroA, aroC, or aroD) in the Salmonella chromosome, rendering the strain auxotrophic for PABA, a substrate that cannot be scavenged in the mammalian cell, such as *Salmonella typhi* strain CVD 908 (Hone et al (1991), supra).

In another embodiment, the above-described objects of the present invention have been met by a vaccine against typhoid fever comprising:

(A) a pharmaceutically effective amount of a *Salmonella typhi* mutant, wherein said mutant constitutively expresses Vi antigen; and (B) a pharmaceutically acceptable carrier or diluent.

In yet another embodiment, the above-described object of the present invention has been met by a live vector vaccine comprising:

(A) a pharmaceutically effective amount of a Salmonella mutant, wherein said mutant constitutively expresses Vi antigen, and wherein said mutant encodes and expresses a foreign antigen under the control of a prokaryotic promoter (i.e., bacterial expression of the foreign antigen); and (B) a pharmaceutically acceptable carrier or diluent.

The particular foreign antigen employed in the Salmonella live vector is not critical to the present invention. The attenuated Salmonella strain(s) of the present invention may be used as a live vector(s) for immunization against enteric pathogens (pathogen defined as bacterial, viral, etc.), sexually transmitted disease pathogens, acute respiratory tract disease pathogens or pathogens with a mucosal entry that lead to grave systemic manifestations of disease (e.g., meningococcal disease). It may also be used to protect against different types of parasitic infections, such as *Plasmodium falciparum,* Leishmania species, *Entameba histolytica* and Cryptosporidium.

Examples of antigens from enteric pathogens that may be expressed in the Salmonella live vectors of the present invention include:

(a) Fimbrial colonization factors of enterotoxigenic *E. coli,* and either the B subunit of heat-labile enterotoxin or a mutant heat-labile enterotoxin (that does not cause intestinal secretion but, elicits neutralizing antitoxin);

(b) Fimbrial antigens and/or intimin of enterohemorrhagic *E. coli,* along with B subunit of Shiga toxin 1 or 2 (or mutant Shiga toxin 1 or 2);

(c) O antigens of Shigella and invasion plasmid antigens or VirG of Shigella;

(d) Neutralization antigens from rotaviruses;

(e) Urease, colonization antigens and other protective antigens from *Helicobacter pilori;* and (f) Inactivated *Clostridium difficile* toxins or antigens derived from them.

Examples of antigens from sexually-transmitted pathogens that may be expressed in the Salmonella live vectors of the present invention include:

(a) Pili and outer membrane proteins of *Neisseria gonorrhoae;* and (b) Proteins of *Chlamydia trachomatis.*

Examples of antigens from acute respiratory tract pathogens that may be expressed in the Salmonella live vectors of the present invention include:

(a) A mutant diphtheria toxin with substitutions in the AND binding domain that lacks toxic activity yet, elicits neutralizing antitoxin;

(b) Antigens of *Bordetella pertussis,* including a fusion protein consisting of the truncated S1 subunit of pertussis toxin fused to fragment C of tetanus toxin, mutant pertussis toxin, filamentous hemagglutinin and pertactin;

(c) F and G glycoproteins of Respiratory Syncytial Virus;

(d) Capsular polysaccharide of *Haemphlus influenzae* type b; and (e) Capsular polysaccharides of group A and C *Neisseria meningitidis,* and outer membrane proteins of group B *N. meningitidis.*

Examples of antigens from parasites that may be expressed in the Salmonella live vectors of the present invention include:

(a) The circumsporozoite protein (CSP), Liver Stage Antigen-1 (LSA-1), SSP-2 (also known as TRAP) and Exp-1 of *Plasmodium falciparum;*

(b) Asexual erythrocytic stage antigens of *P. falciparum,* including MSP-1, MSP-2, SERA, AMA-1 and SREHP;

(c) Sexual stage antigens of *P. falciparum,* including Pfs25, and gp63 of Leishmania species; and (d) The serine-rich *Entameba histolytica* protein (SREHP).

In still another embodiment, the above-described objects of the present invention has been met by a DNA-mediated vaccine comprising:

(A) a pharmaceutically effective amount of a Salmonella mutant, wherein said mutant constitutively expresses Vi antigen, and wherein said mutant contains a plasmid which encodes and expresses, using a eukaryotic promoter, in a eukaryotic cell, a foreign antigen; and (B) a pharmaceutically acceptable carrier or diluent.

Details as to the construction and use of DNA-mediated vaccines can be found in U.S. patent application Ser. No. 08/433,790, filed May 3, 1995, now U.S. Pat. No. 5,877,159 which is incorporated by reference herein in its entirety.

The particular foreign antigen employed in the DNA-mediated vaccine is not critical to the present invention. Examples of such antigens include those from a diversity of pathogens, such as influenza (Justewicz et al, *J. Virol.,* 69:7712–7717 (1995); and Fynan et al, *Int. J. Immunopharmacol.,* 17:79–83 (1995)), lymphocytic choriomeningitis virus (Zarozinski et al, *J. Immunol.,* 154:4010–4017 (1995)), human immunodeficiency virus (Shiver et al, *Ann. NY. Acad. Sci.,* 772:198–208 (1995)), hepatitis B virus (Davis et al, *Vaccine,* 12:1503–1509 (1994)), hepatitis C virus (Lagging et al, *J. Virol.,* 69:5859–5863 (1995)), rabies virus (Xiang et al, *Virology,* 209:569–579 (1995)), Schistosoma (Yang et al, *Biochem. Biophys. Res. Commun.,* 212:1029–1039 (1995)), Plasmodium (Sedegah et al, *Proc. Natl. Acad. Sci., USA,* 91:9866–9870 (1994)); and mycoplasma (Barry et al, *Nature,* 377:632–635 (1995)).

The decision whether to express the foreign antigen in Salmonella (using a prokaryotic promoter in a live vector vaccine) or in the cells invaded by Salmonella (using a eukaryotic promoter in a DNA-mediated vaccine) may be based upon which vaccine construction for that particular antigen gives the best immune response in animal studies or in clinical trials, and/or, if the glycosylation of an antigen is essential for its protective immunogenicity, and/or, if the correct tertiary conformation of an antigen is achieved better with one form of expression than the other.

In the vaccines of the present invention, the pharmaceutically effective amount of the mutants of the present invention to be administered may vary depending on the age, weight and sex of the subject, and the mode of administration. Generally, the dosage employed will be about $10^2$ cfu to $10^{10}$ cfu. Preferably, about $10^6$ cfu to $10^9$ cfu is used for an oral administration in which the vaccine is given in capsules or resuspended in a buffer solution to protect the attenuated bacteria against the acidic pH in the stomach; or about $10^2$ cfu to $10^7$ cfu is used for intranasal administration in which the bacteria is given in drops or in aerosol.

The particular pharmaceutically acceptable carrier or diluent employed is not critical to the present invention, and are conventional in the art. Examples of diluents include: buffers for buffering against gastric acid in the stomach, such as citrate buffer (pH 7.0) containing sucrose, bicarbonate buffer (pH 7.0) alone (Levine et al, (1987b) supra; and Black et al, supra), or bicarbonate buffer (pH 7.0) containing ascorbic acid, lactose, and optionally aspartame (Levine et al, *Lancet,* II:467–470 (1988)). Examples of carriers include: proteins, e.g., as found in skim milk; sugars, e.g., sucrose; or polyvinylpyrrolidone.

The mutants of the present invention can be stored at −70° C. while suspended in Luria broth (DIFCO) containing 30%–50% (v/v) glycerol.

The following examples are provided for illustrative purposes only, and are in no way intended to limit the scope of the present invention.

EXAMPLE 1

Construction of ΔguaB–A *S. typhi* Strains

A. Construction of the ΔguaB–A Deletion Cassette pJW101

DNA segments that include the 5' terminus of the guaB gene, and the 3' terminus of the guaA gene were amplified by PCR using *S. typhi* strain Ty2 genomic DNA as template, and then fused in a second PCR reaction, thereby giving rise to the ΔguaB–A allele (FIG. 4). The methods used in the construction of the ΔguaB–A allele were analogous to those described in the construction of the ΔguaB–A allele in ΔguaB–A *S. flexneri* 2a strain CVD 1204 (Noriega et al (1996), supra; and U.S. patent application Ser. No. 08/629,600, filed Apr. 9, 1996 (published as U.S. Pat. No. 5,783,196), which is incorporated by reference herein in its entirety).

In the first PCR reaction (FIG. 4) the primers used to amplify the 5' terminus of the guaB–A allele were: 5'-CGAGCTCGC GAGCTCGGTAAAGTACCAGTGACCGGAAGCTGGTTGCGT-3' (SEQ ID NO: 2); and 5'-GGGCCCGGG GGATCCTCAACCGACGCCAGTCACGATACGAGTTGTACAGAT-3' (SEQ ID NO: 3); and the primers used to amplify the 3' terminus of the ΔguaB–A allele were: 5'-TGAGGATCCCCC GGGCCCGGCTACGCGCAGGTTGAAGTCGTAAACGACAGC-3' (SEQ ID NO: 4); and 5'-GCTCTAGAGC TCTAGAGCTCATTCCCACTCAATGGTAGCTGGCGGCTT-3' (SEQ ID NO: 5).

Within the internal primers (SEQ ID NOS: 3 and 4) were introduced an in-frame stop signal codon (TGA and TCA) upstream of two unique restriction sites (ApaI and BamHI) (underlined) that were added for the introduction of foreign genes into the chromosomal ΔguaB–A allele. The stop signal avoids translational fusions of the ΔguaB with ΔguaA products, or of the ΔguaB product with the products of foreign genes inserted in the middle of the ΔguaB–A allele. In addition, these internal primers introduced sequences that served as the homologous region (in bold) with which the 5' and 3' PCR products were fused in a second PCR reaction (thus forming the ΔguaB–A allele) (FIG. 4).

In the second PCR reaction, the 5' and 3' segments were fused using the extreme primers (SEQ ID NOS: 2 and 5), and the resulting fusion product was amplified in the same reaction. In this reaction, the given homologous region (ApaI-BamHI) annealed, effectively fusing the 5' and 3' segments, which at that time may have acted as their own primers and/or templates for the Taq polymerase, depending upon which strands of DNA were annealed. To facilitate this fusion, a PCR-program was designed in which the first 15 cycles had an annealing temperature slope (1° C./8 sec from 40° C. to 50° C.+50° C. for 2 min), followed by 15 cycles with an annealing temperature of 55° C. in which the new ΔguaB–A allele was amplified. Thus, there were 900 base pairs of the guaB–A operon that were not amplified, giving rise to ΔguaB–A (FIG. 4).

The extreme primers (SEQ ID NOS: 2 and 5) were designed to introduce unique restriction sites (SstI and XbaI) (underlined) that were used to clone the ΔguaB–A allele into unique restriction sites in the temperature-sensitive, pSC101-based (Blomfield et al, *Mol. Microbiol.,* 5:1447–1457 (1991)) suicide plasmid pFM307A, giving rise to plasmid pFM307::ΔguaB–A. Plasmid FM307A (6.3 Kbp) was constructed by substituting a 4.3 Kbp NaeI—NaeI fragment, containing the cam gene (chloramphenicol resistance) in pIB307 (Blomfield et al, supra) with a 3.8 Kbp BamHI—BamHI fragment (blunt-ended by Klenow polymerase) containing the SacB-Kan cassette (providing resistance to kanamycin and sucrose counter-selection) from pIB279 (Blomfield et al, supra). In addition, it was considered advantageous to insert a non-antibiotic selection marker into the middle of the ΔguaB–A allele in order to:

(i) facilitate the exchange of the ΔguaB–A for the proficient guaB–A allele in Ty2; and (ii) provide a selection marker that would allow the identification of the vaccine strain in the field.

Thus, next, the 5.0 Kbp arsenic resistance (ars) operon of R factor R773 was obtained as a HindIII fragment from pUM1 (Chen et al, *J. Bacteriol.,* 161:758–763 (1985)) (kindly provided by Dr. Rosen, Wayne State University, Detroit, Mich.), and cloned under the regulation of the $P_{tac}$ promoter in pKK223-3 (Pharmacia, Piscataway, N.J.). Then, a (blunt-ended) $P_{tac}$-ars NaeI-DraI segment was obtained, and cloned in the ApaI site (blunt-ended by T4 polymerase) of the ΔguaB–A allele in pFM307::ΔguaB–A, yielding pJW101 (FIG. 4).

B. Suicide Deletion Cassette-Driven Mutations pJW101 was used to introduce the ΔguaB–A::$P_{tac}$-ars allele therein into wild-type *S. typhi* strain Ty2 by homologous recombination, as described by Blomfield et al, supra; Noriega et al (1995), supra, and Noriega et al (1996), supra with the exception that 6.0 μM sodium arsenite (SIGMA) was present in the media throughout the procedure.

C. Screening of Mutants by DNA Probes and PCR

Candidate bacterial clones were grown at 37° C. overnight in a grid pattern on Luria agar plates supplemented with 6.0 μM sodium arsenite or in minimum medium. Colonies growing on the arsenite-supplemented L agar, but not growing in minimum medium, were then transferred to No. 541 filter paper (Whatman, Maidstone, England), and blotted as described by Gicquelais et al, *J. Clin. Microbiol.,* 28:2485–2490 (1990), and probed using a $\gamma P^{32}$-labeled 40 bp oligonucleotide: 5'-GGGCGGCCTGCGCTCCTGTATGGGTCTGACCGGCTGTGGT-3' (SEQ ID NO: 6), corresponding to a deleted portion of the guaB–A wild-type allele (negative probe). Clones that failed to hybridize with the $\gamma P^{32}$-labeled 40 bp oligonucleotide probe were selected. The ΔguaB–A S. typhi clones were not able to grow in minimal medium unless supplemented with 10 mg of guanine/l.

The deletion mutation in the guaB–A operon and the $P_{tac}$-ars insertion in the ΔguaB–A allele was confirmed by Southern blot hybridization with a $P^{32}$-labeled ΔguaB–A operon, ars operon, and the above-describe guaB–A negative probe. One ΔguaB–A S. typhi clone was arbitrarily selected and named CVD 915. Strain CVD 915 was deposited at the American Type Culture Collection on May 4, 1998, under ATCC No. 202115.

Strain CVD 915 is routinely grown with 6.0 μM of sodium arsenite in the medium but, no growth is obtained at this concentration of arsenite with strain Ty2, or with any other strain of Salmonella, Shigella or E. coli tested.

EXAMPLE 2
Invasion and Intracellular Growth in Tissue Cultures

Invasion and intercellular growth were assayed using gentamicin protection assays, which were performed with slight modifications to methods previously described by Tartera et al, Infect. Immun., 61:3084–3089 (1993). Briefly, semiconfluent Henle 407 cell monolayers on 24-well plates were infected in triplicate wells with either wild-type strain Ty2; ΔguaB–A CVD 915; ΔaroC, ΔaroD CVD 908 or ΔaroC, ΔaroD, Δhtr CVD 908-htrA at a 50:1 ratio, for 90 min, after which extracellular organisms were killed with 100 μg/ml of gentamicin for 30 min, washed (0 hrs time point), and thereafter incubated with 20 μg/ml of gentamicin. At 0 hr, 4 hr and 22 hr thereafter, triplicate infected tissue culture monolayers were lyzed with sterile water and serial dilutions of that suspension cultured overnight, at 37° C., on LB agar supplemented with 10 μg of guanine per liter. The results are shown in Table 2 below.

TABLE 2

Invasion and Intracellular Growth in Henle 407 Cells

| Strain | Genotype | Intracellular cfu[a] | | |
|---|---|---|---|---|
| | | 0 hr | 4 hr | 22 hr |
| Ty2 | wild-type | $6.7 \times 10^3$ | $3.1 \times 10^4$ | $8.8 \times 10^4$ |
| CVD 915 | ΔguaB–A | $3.3 \times 10^2$ | $2.9 \times 10^2$ | $2.5 \times 10^2$ |
| CVD 908 | ΔaroC, ΔaroD | $5.8 \times 10^2$ | $1.3 \times 10^3$ | $3.5 \times 10^3$ |
| CVD 908-htrA | ΔaroC, ΔaroD, ΔhtrA | $1.3 \times 10^3$ | $3.4 \times 10^3$ | $1.3 \times 10^3$ |

[a]Colony forming units

As shown in Table 2 above, strain CVD 915 had an invasion capability and intracellular growth that was significantly lower than that exhibited by wild-type strain Ty2, and comparable to that exhibited by strain CVD 908-htrA. That is, as shown in Table 2 above, in two different experiments, wild-type S. typhi strain Ty2 efficiently invaded Henle 407 cells, and replicated in them over 13-fold in a 22 hr period. The ΔaroC, ΔaroD strain CVD 908 consistently had fewer intracellular generations, i.e., 6-fold, at 22 hr. Also as shown in Table 2 above, the mutant strain ΔguaB–A CVD 915 was significantly less invasive for Henle cells than its wild-type parent or the strains CVD 908 and CVD 908-htrA, and its intracellular growth, i.e., 0-fold, was equivalent to that of the CVD 908-htrA mutant.

EXAMPLE 3
Comparative Safety of Vaccine Candidate Strains Ty21A, CVD 908 and CVD 915

The attenuation of ΔguaB–A S. typhi strain CVD 915 was ascertained with respect to wild-type strain Ty2, and other attenuated strains, using the murine hog-mucin assay (Powell et al, J. Biolog. Standar., 8:79–85 (1980)). Briefly, mice were inoculated intraperitoneally with various ten-fold dilutions of the different strains suspended in 0.5 ml of 10% (w/v) hog mucin. Subsequently, the mice were followed up for mortality occurring within 72 hr after inoculation, and the $LD_{50}$ of the different groups calculated by analysis of their linear regression. The results are shown in Table 3 below.

TABLE 3

| Strain | $LD_{50}$ in cfu |
|---|---|
| Ty2 | $1.4 \times 10^2$ |
| CVD 908 | $4.4 \times 10^6$ |
| CVD 915 | $7.7 \times 10^7$ |
| Ty21a | $1.9 \times 10^8$ |

As shown in Table 3 above, strain CVD 915 had an estimated $LD_{50}$ that was over 5-logs above that obtained with wild-type strain Ty2, and between that obtained by the ΔaroC, ΔaroD mutant strain CVD 908 and the chemically mutagenized, non-invasive, strain Ty21a.

EXAMPLE 4
Use of Strain CVD 915 as a Live Vector for Delivering Foreign Proteins and DNA Vaccine Plasmids for Expressing Foreign Antigens in Eukaryotic Cells A mouse model of intranasal immunization with a genetically-engineered ΔaroC, ΔaroD strains of S. typhi (CVD 908) carrying fragment C of tetanus toxin (fragment C of TT) has been described by Galen et al, Vaccine, 15:700–708 (1997). The constructs which were assayed in this model included CVD 908 carrying plasmids encoding unfused fragment C of TT under the control of an anaerobically-activated prokaryotic promoter derived from nirB or the powerful constitutive promoter lpp. It was observed that:

(i) intranasal immunization of mice with these constructs resulted in high titers of neutralizing anti-TT serum IgG antibodies;

(ii) immunized mice were protected against a challenge with one hundred 50% lethal doses of TT that killed all control mice; and (iii) that cells obtained from the spleens and cervical regional lymph nodes of intranasally immunized mice 6 weeks after immunization showed significant proliferative responses to S. typhi (Hd flagella and phenol-inactivated whole-cell S. typhi particles), as well as to fragment C of TT and TT antigens.

These investigations have been extended below by studying the immunogenicity in mice of novel attenuated strains of S. typhi carrying plasmids containing genes encoding foreign antigens (i.e., fragment C of TT) under the control of prokaryotic or eukaryotic promoters.

A. Immunological Responses Elicited by Immunization with Attenuated Strains of S. typhi Carrying Prokaryotic and Eukaryotic Expression Vectors Encoding Fragment C of TT Following the observation that immune responses can be elicited by direct immunization with plasmid DNA (Ulmer et al, Science, 259:1745–1749 (1993)), several nucleic acid vectors encoding foreign antigens have been evaluated as vaccines. DNA vaccination has been shown to elicit high levels of both humoral and cell-mediated immune responses using plasmids encoding many viral antigens, including NP of influenza A virus (Ulmer et al, supra). Since this early observation, several nucleic acid vectors encoding foreign antigens have been evaluated as vaccines. In particular, DNA-vaccination has been very extensively studied using influenza virus antigens. Protective immune responses have been induced in mice (Fynan et al, *Proc. Natl. Acad. Sci., U.S.A.,* 90:11478–11482 (1993a); Justewicz et al (1995), supra; and Justewicz et al, *Virol.,* 224:10–17 (1996)), ferrets (Webster et al, *Vaccine,* 12:1495–1498 (1994)), chickens (Fynan et al, *DNA Cell Biol.,* 12:785–789 (1993b); and Fynan et al (1993a), supra) and nonhuman primates (Donnelly et al, *Nat. Med.,* 1:583–587 (1995)) following intramuscular (i.m.) or epidermal (gene gun) immunization with eukaryotic expression vectors encoding influenza virus antigens. Immune responses against several other antigens from other viruses (Cox et al, supra; Davis et al (1996a), supra; Donnelly et al, supra; Lagging et al, supra; Wang et al, *Virol.,* 211:102–112 (1995); and Zarozinski et al, supra); parasites (Doolan et al, *J. Exp. Med.,* 183:1739–1746 (1996); Gardner et al, *J. Pharm. Sci.,* 85:1294–1300 (1996); Hoffman et al, *Vaccine,* 12:1529–1533 (1994); Sedegah et al, supra; and Yang et al, supra); bacteria (Anderson et al, *Infect. Immun.,* 64:3168–3173 (1996); Barry et al, supra; Huygen et al, *Nat. Med.,* 2:893–898 (1996); Luke et al, *J. Infect. Dis.,* 175:91–97 (1997); and Tascon et al, *Nat. Med.,* 2:888–892 (1996)); and tumor cells (Conry et al, *Cancer Res.,* 54:1164–1168 (1994); Conry et al (1995), supra; and Wang et al, *Human Gene Therapy,* 6:407–418 (1995)) have also been induced by DNA vaccination in various animal models. These studies have increased the understanding of the nature of the immune response elicited by DNA-vaccines. For example, strong antibody responses have been elicited in mice against the Hepatitis B surface antigen (HBsAg) following a single i.m. immunization with a plasmid encoding this antigen (Davis et al, *Hum. Mol. Genet.,* 2:1847–1851 (1993); and Michel et al, *Proc. Natl. Acad. Sci., U.S.A.,* 92:5307–5311 (1995)). In these studies, peak IgG titers were observed 4–8 weeks following immunization, which persisted at high levels for 6 months. DNA-vaccines encoding this antigen have also been shown to be effective in eliciting antibody and MHC class 1 restricted CTL responses in mice that are not responsive to purified HBsAg (Davis et al (1996b), supra; and Schirmbeck et al, *J. Virol.,* 69:5929–5934 (1995)). Thus, at least in the case of HBsAg, DNA-vaccination has been shown to overcome genetic restriction in mice, and induce a more persistent immune response than parenteral immunization with purified proteins.

Tetanus toxin (TT) is a potent neurotoxin synthesized by *Clostridium tetani.* Protective immunity against tetanus in man and animals is correlated with the titer of TT neutralizing antibodies in serum (Bizzini, *In: Clostridium Tetani,* Gyles et al (Eds.), Iowa State University Press, Ames, IA, pages 97–105 (1993); and Habig et al, *Vaccines and Immunotherapy,* Cryz (Ed.), Pergamon, N.Y., pages 13–19 (1991)). Thus, good protection against tetanus can be induced by parenteral immunization with inactivated TT or non-toxic derivatives. Measurement of the potency of such vaccine preparations is a well-established procedure, and is described by the European and British Pharmacopoeias (Coster et al, *Lancet,* 345:949–952 (1995); and Sanchez et al, *Trans. R. Soc. Trop. Med. Hyg.,* 89:542–545 (1995)). The level of anti-tetanus antibody is traditionally determined by toxin neutralization assays in mice. Recently, sensitive ELISA assays have been developed which are less time consuming and expensive but, correlate well with the toxin neutralization test (Manghi et al, *J. Immunol. Methods,* 168:17–24 (1994); and Melville-Smith, *In: Diptheria and Tetanus Antitoxins,* Wreghitt et al (Eds.), ELISA in the Clinical Microbiology Laboratory, Public Health Laboratory Service, London, pages 136–147 (1990)). Titers of anti-toxin antibody in the sera are normally determined in IU/ml (where 0.1 IU/ml in human sera is sufficient to protect against TT challenge) by comparison with an international standard anti-TT sera (WHO). Thus, vaccine potency (expressed in IU/ml) can be compared for different TT vaccine preparations. At present, vaccine preparations against tetanus are produced by formaldehyde inactivation of TT from *C. tetani,* which is a time consuming, and technically demanding procedure. This has prompted a search for alternative detoxified preparations of TT as vaccines.

TT consists of a 150 kDa protein containing a 50 kDa light (L) chain disulphide bonded to a 100 kDa heavy (H) chain (Helting et al, *J. Biol. Chem.,* 252:187–193 (1977a); and Niemann et al, Molecular Biology of Clostridial Neurotoxins, Alouf Ed., Sourcebook of Bacterial Protein Toxins, Academic Press, London (1991)). The toxic activity of this protein lies within the L chain, a zinc-dependent protease (Schiavo et al, *EMBO J.,* 11:3577–3583 (1992)), which is thought to mediate the blockage of inhibitor release from neurons by proteolysis of synaptobrevin (Schiavo et al, *Nature (London),* 359:832–835 (1992)). The H chain is thought to initiate binding and uptake of the toxin at presynaptic membranes (Helting et al, *J. Biol. Chem.,* 252:194–197 (1977b); and Morris et al, *J. Biol. Chem.,* 255:6071–6076 (1980)). Digestion of the toxin molecule with papain yields a 50 kDa polypeptide, which corresponds to the C-terminal of the H-chain and a 100 kDa molecule corresponding to the L chain linked to the N-terminal of the H chain (Helting et al (1977a), supra). The 50 kDa polypeptide, termed TT fragment C (FC), is non-toxic but, possesses ganglioside (Halpern et al, *Infect. Immun.,* 58:1004–1009 (1990); and Morris et al (1980), supra) and protein binding activities (Schiavo et al, *FEBS. Lett.,* 290:227–230 (1991)). In early studies, vaccination of animals with FC derived by proteolysis of the native toxin was shown to protect them against subsequent lethal challenge with TT (Helting et al (1977a), supra). Furthermore, studies with monoclonal antibodies demonstrated that neutralizing epitopes exist within this molecule (Kenimer et al, *Infect. Immun.,* 42:942–948 (1983)). Thus, FC was identified as a good candidate molecule for the production of an alternative TT vaccine.

Recent data have indicated that intramuscular immunization with a plasmid encoding fragment C of TT under the control of the CMV promoter/enhancer region (pcDNA3/tetC) elicited high anti-fragment C serum antibody titers, proliferative responses and interferon-γ production. Moreover, it was shown that these mice were protected against a lethal challenge with TT (Anderson et al, supra).

In an effort to further explore whether the immunogenicity and protective capacity of pcDNA3/tet can be optimized, a series of studies were initiated to deliver this construct to the host by attenuated strains of *S. typhi.* This approach has the potential to provide a new delivery system for DNA-mediated vaccines against bacterial and other infectious diseases.

A description of these studies, including construction of pcDNA3/tetC is set forth below.

1. Gene Encoding Fragment C of TT

The sequence of the gene encoding TT has been described in the art (Eisel et al, *EMBO J.,* 5:2495–2502 (1986);

Fairweather et al, *J. Bacteriol.*, 165:21–27 (1986); and Fairweather et al, *Nucleic. Acids Res.*, 14:7809–7812 (1986)). Plasmid vectors encoding native fragment C sequence under the control of $P_{tac}$ were previously shown to express FC in *E. coli* at a low level (3–4% tcp) (Makoff et al, *Bio/Technology,* 7:1043–1046 (1989)). In order to increase the level of expression, the codon usage of the native fragment C gene (which is A-T rich) was optimized for *E. coli.* The resulting 99% synthetic fragment C gene (tetC) directed expression at higher levels (11–14% tcp) in *E. coli* (Makoff et al, *Nucleic. Acids Res.,* 17:10191–10202 (1989)). This prompted the investigation of other expression systems as a means of producing large amounts of fragment C for vaccination. Preparations of recombinant fragment C purified from yeast cells (Clare et al, *Biotechnology* (*N.Y.*), 9:455–460 (1991); and Romanos et al, *Nucleic. Acids Res.,* 19:1461–1467 (1991)), and cultured insect cells (Charles et al, *Infect. Immun.,* 59:1627–1632 (1991)), have now also been shown to induce protective immune responses against tetanus toxin following parenteral immunization. Interestingly, as was the case with *E. coli,* the native *C. tetani* gene encoding fragment C could not be expressed in *Saccharomyces cerevisiae,* whereas the codon optimized gene from pTETtac115 was expressed by this organism. The synthetic fragment C gene that had been codon optimized for expression in *E. coli* therefore, appeared to have been fortuitously optimized for expression in eukaryotes.

2. Construction of pTETnir15

Constitutive high level expression of foreign antigens in vivo can result in the loss of the antigen-encoding plasmid, impairing the ability of the carrier strain to deliver the antigen to the immune system. Consequently, several approaches have been used to maintain plasmid stability in vivo. One such approach is the use of in vivo inducible promoters, such as the nirB promoter. This promoter was originally defined in *E. coli,* where it controls the expression of an operon which includes the NADH-dependent nitrate reductase gene, nirB. It is regulated by nitrates, and changes in the oxygen tension of the environment, the peak activity being achieved under anaerobic conditions. A modified version of the nirB promoter has been constructed which is induced when bacterial cells grow in an atmosphere of limited oxygen availability or enter eukaryotic cells in vitro. Homologous Col-E1 based plasmids, which express fragment C from the nirB and tac promoters respectively, have been constructed. These strains were shown to induce protection against challenge with TT following oral immunization. However, two doses of the tac based strain were required to ensure complete protection, whereas only one dose of the strain expressing fragment C using the nirB promoter was required. Thus, the nirB construct proved more persistent and stable in vivo than the tac construct (Chatfield et al, *Biotechnology,* 10:888 (1992b)).

3. Construction of pcDNA3/tetC

The construction and characterization of plasmid pcDNA3/tetC was carried out as described by Anderson et al, supra, which is incorporated by reference herein in its entirety (see FIG. 5).

4. Immunization with *S. typhi* CVD 915 Harboring pcDNA3/tetC or pTETnir15

As discussed above, studies were initiated to evaluate the capacity of attenuated strains of *S. typhi* to deliver prokaryotic and eukaryotic expression vectors encoding foreign antigens, e.g., fragment C of TT, to the mammalian immune system and induce protective immune responses. To compare this system with the traditional naked DNA immunization, the response elicited by the naked pcDNA3/tetC vector was also evaluated.

To this end, pcDNA3/tetC or pTETnir15 plasmids were electroporated into CVD 915. The structure of the purified plasmids was confirmed by separating restriction endonuclease digestion products of the plasmids in agarose gels: pcDNA3 and pcDNA3/tetC with HindIII and XbaI; and pTETnir15 with EcoRI and BamHI. Expression of fragment C was confirmed by SDS-PAGE, and immunobloting. Bacterial samples were grown to stationary phase and 1.0 ml aliquots were harvested by centrifugation, and resuspended in 200 $\mu$l of SDS-sample buffer. These samples were then subjected to SDS-PAGE and Western blotting. Anti-fragment C mAb and horse radish peroxidase conjugated-goat anti-mouse were used as first and second antibodies, respectively. Each sample was loaded at approximately $1.0\times10^8$ cfu/well.

The intranasal route was used for the live vector (CVD 915) carrying both plasmids (CVD 915 (pcDNA3/tetC) and CVD 915 (pTETnir15)), and the intramuscular route was used for naked DNA immunization (pcDNA3/tetC) Balb/c mice were immunized according to the protocol shown in Table 4 below:

TABLE 4

| Group | Number of Mice | Immunogen | Route of Immunization | First Dose | Second Dose |
|---|---|---|---|---|---|
| 1 | 10 | CVD 915 (pcDNA3/tetC) | Intranasal | $5.9 \times 10^9$ cfu | $11 \times 10^9$ cfu |
| 2 | 10 | CVD 915 (pTETnir15) | Intranasal | $5.0 \times 10^9$ cfu | $6.3 \times 10^9$ cfu |
| 3 | 10 | CVD 915 | Intranasal | $6.5 \times 10^9$ cfu | $5.25 \times 10^9$ cfu |
| 4 | 10 | pcDNA3/tetC | Intramuscular | 98 $\mu$g | 95 $\mu$g |
| 5 | 5 | PBS | Intranasal | 25 $\mu$l | 5.0 $\mu$l |

5. Antibody Responses

Animals were bled from the retroorbital vein according to the following schedule:

(a) Before immunization (b) 14 days after immunization 36 days after immunization (c) 14 days after boost 28 days after boost 42 days after boost 56 days after boost (sacrifice)

Total IgG anti-fragment C serum antibodies were measured by ELISA. Briefly, recombinant fragment C was used for coating the ELISA plates with antigen at 4.0 $\mu$g/ml. Sera were titrated in eight two-fold dilutions. Antibody levels are expressed in International Units by comparison with a previously calibrated standard sera. Standard sera was prepared by immunizing mice with adsorbed tetanus toxoid four times at biweekly intervals. Sera were pooled and titrated by an in vivo neutralization test in mice according to the procedure described in the European Pharmacopoeia. The number of international neutralizing units were determined in parallel with the International Standard of Tetanus Antitoxin. The results are shown in FIG. 6.

As shown in FIG. 6, although slightly higher levels of antibodies appeared to be elicited by the CVD 915 (pcDNA3/tetC) construct, very high levels of anti-fragment C serum antibodies (1,000 to 2,000-fold the protective anti-TT antibody level in humans) were observed after immunization and a single boost with both CVD 915 (pTETnir15) or CVD 915 (pcDNA3/tetC) constructs. The observed anti-fragment C serum antibody levels of up to 20 IU/ml corresponded to end dilution titers of approximately 1:50,000. In contrast, relatively modest levels of anti-fragment C serum antibodies (approximately 50-fold the protective anti-TT levels in humans) were observed in mice immunized with naked pcDNA3/tetC. Anti-fragment C serum antibody levels reached maximal levels 50 days after the primary immunization, and remained at the same levels up to 92 days after the primary immunization, the last time point studied. No responses were observed in mice immunized with CVD 915 alone.

6. Cell-Mediated Immune Responses: Proliferation Assays

Ninety-two days after immunization, pools of single cell suspensions were prepared from cervical lymph nodes, mesenteric lymph nodes and spleens from the 5 to 7 mice remaining in each of the above-discussed groups. A pool of cells was also prepared from inguinal lymph nodes obtained from the mice immunized i.m. with naked pcDNA3/tetC. The following average cell yields were obtained:

Cervical lymph nodes: $6.6 \times 10^6$ cells/mouse
Mesenteric lymph nodes: $10.1 \times 10^6$ cells/mouse
Inguinal lymph nodes: $1.6 \times 10^6$ cells/mouse
Spleens: $52.5 \times 10^6$ cells/mouse Proliferation assays were performed by resuspending the cells in complete RPMI media (RPMI containing 10% (v/v) fetal calf serum, glutamine and antibiotics), and incubated at $2.0 \times 10^5$ cells/well in triplicate in 96-well round bottom plates in the absence or presence of antigen. The following soluble antigens were used in these studies: Bovine Serum Albumin (BSA), fragment C of TT and highly purified S. typhi flagella, at 0.02, 0.2 and 2.0 µg/ml. After five days of incubation at 37° C., 5% $CO_2$, the cultures were pulsed with $^3$H-thymidine, and the cultures terminated 18 hrs later by automatic harvesting. Thymidine incorporation was determined by liquid scintillation counting. The results, which are shown in FIGS. 7 and 8, are expressed as stimulation index (S.I.).

Figure 7:
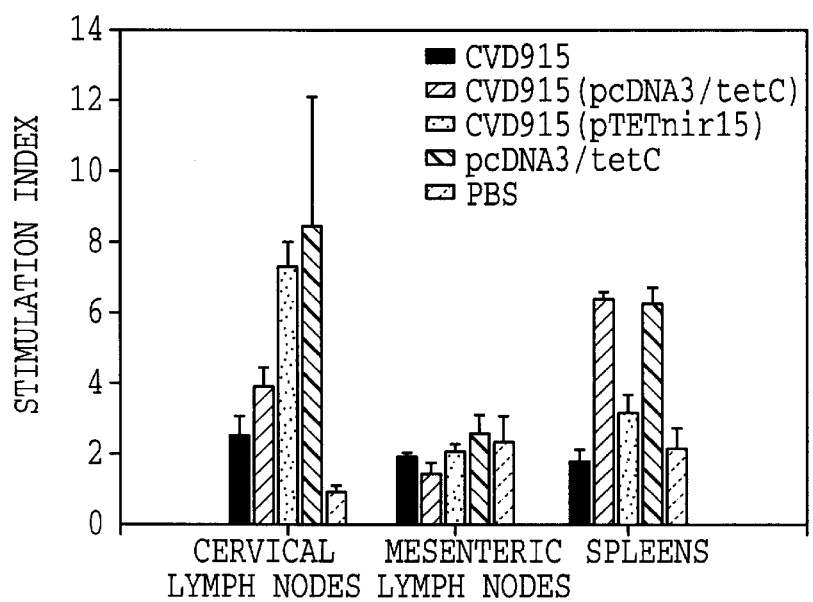
FIG. 7 shows the murine lymphocyte proliferative response against fragment C of tetanus toxin after intranasal immunization with strain ΔguaB–A CVD 915 alone, or as a vector expressing fragment C of tetanus toxin or carrying an eukaryotic expression cassette encoding fragment C of tetanus toxin.

As shown in FIG. 7, immunization with CVD 915 (pTETnir15) and CVD 915 (pcDNA3/tetC) constructs, as well as the pcDNA3/tetC naked DNA vaccine, elicited the appearance of sensitized lymphoid cells that proliferated in response to fragment C of TT. These proliferative responses were observed in cell populations isolated from cervical lymph nodes and spleens, but not in those isolated from mesenteric lymph nodes. Specific proliferative responses were also observed to TT. No significant proliferative responses to fragment C of TT (>3 S.I.) were observed in cells isolated from mice immunized with CVD 915 or PBS.

Figure 8:
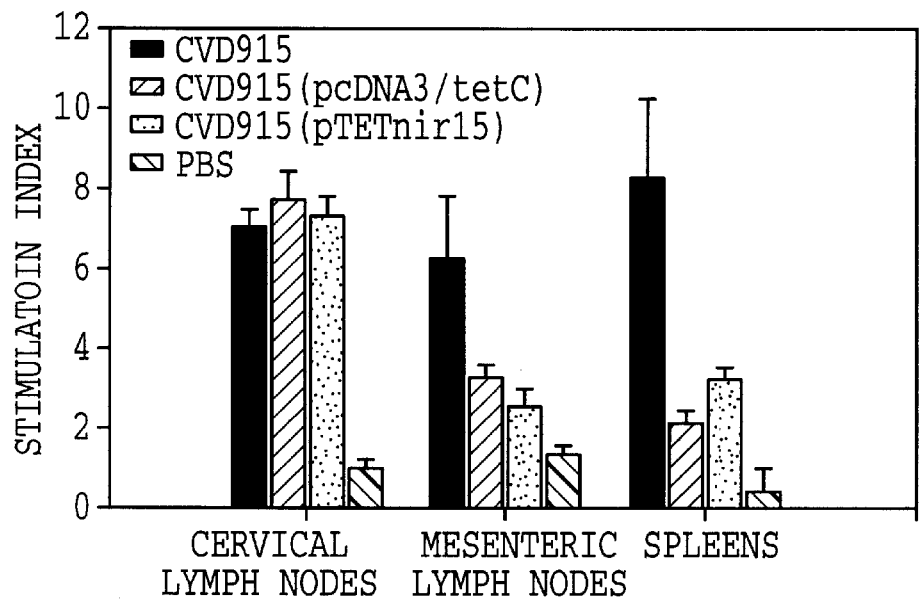
FIG. 8 shows the murine lymphocyte proliferative response against *S. typhi* flagella after intranasal immunization with strain ΔguaB–A CVD 915 alone, or as a vector expressing fragment C of tetanus toxin or carrying an eukaryotic expression cassette encoding fragment C of tetanus toxin.

As shown in FIG. 8, proliferative responses to S. typhi flagella were observed in cell populations isolated from mice immunized with CVD 915, CVD 915 (pTETnir15) and CVD 915 (pcDNA3/tetC) constructs. Also, as shown in FIG. 8, these responses were observed in all populations isolated from mice immunized with CVD 915, and in lymphoid cells isolated from cervical lymph nodes from mice immunized with CVD 915 (pTETnir15) and CVD 915 (pcDNA3/tetC) constructs. Considerably lower proliferative responses were also observed in splenocytes and mesenteric lymph node cells isolated from mice immunized with CVD 915 (pTETnir15) and CVD 915 (pcDNA3/tetC) constructs. Due to technical difficulties, no data is available on the proliferative responses of mice immunized with pcDNA3/tetC naked DNA vaccine to S. typhi flagella. Interestingly, cells isolated from inguinal lymph nodes from mice immunized i.m. with naked pcDNA3/tetC did not show specific proliferative responses to any of the antigens tested. No proliferative responses were observed to BSA in any of the groups tested.

7. Comparison of Serum IgG Anti-Salmonella LPS and S. typhi Flagella Induced by Intranasal Immunization with CVD 915 and CVD 908-htrA One of the important issues to address during the evaluation of new candidate vaccine vectors is to compare the immune responses elicited by the new constructs (e.g., CVD 915) to that of the leading candidates (e.g., CVD 908-htrA) for which a large body of data is already available. With this objective, groups of 10 Balb/C mice were immunized intranasally with $10^{10}$ cfu of either attenuated strain CVD 915 or CVD 908-htrA, twice, 36 days apart. Mice were bled before immunization (day 0) and at days 35, 55 and 95 (CVD 915 only). Antibodies against LPS and flagella antigens were determined by ELISA as described by Tacket et al (1977), supra. Briefly, ELISA plates were coated with 5.0 µg of each antigen, sera samples were tested in 8 2-fold dilutions, antibody titers were expressed as ELISA units/ml defined as the inverse of the dilution that produce 0.5 absorbance values at 492 nm. The results are shown in FIGS. 9 and 10.

Figure 9:
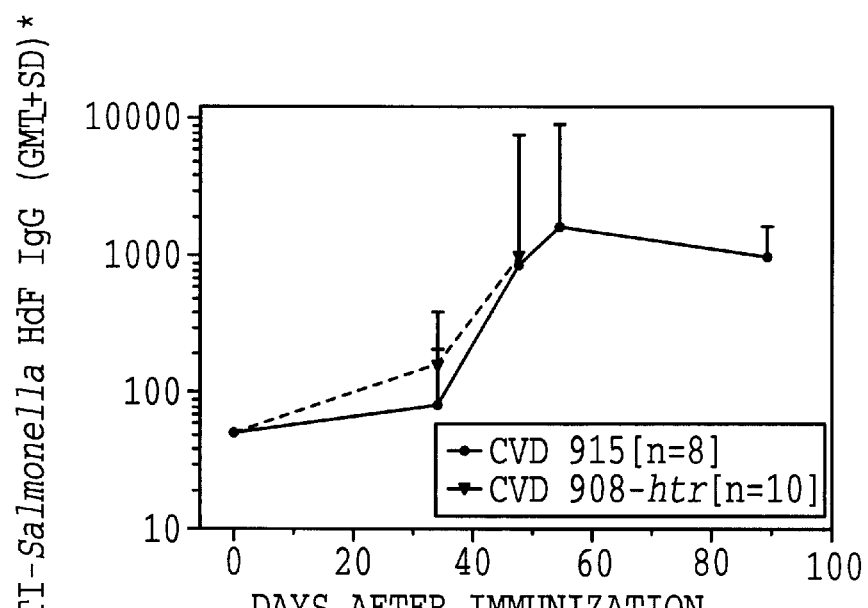
FIG. 9 shows the anti-S. typhi flagella antibody response in mice after intranasal immunization with strain ΔguaB–A S. typhi CVD 915 or strain ΔaroC, ΔaroD, ΔhtrA S. typhi CVD 908-htrA.
Figure 10:
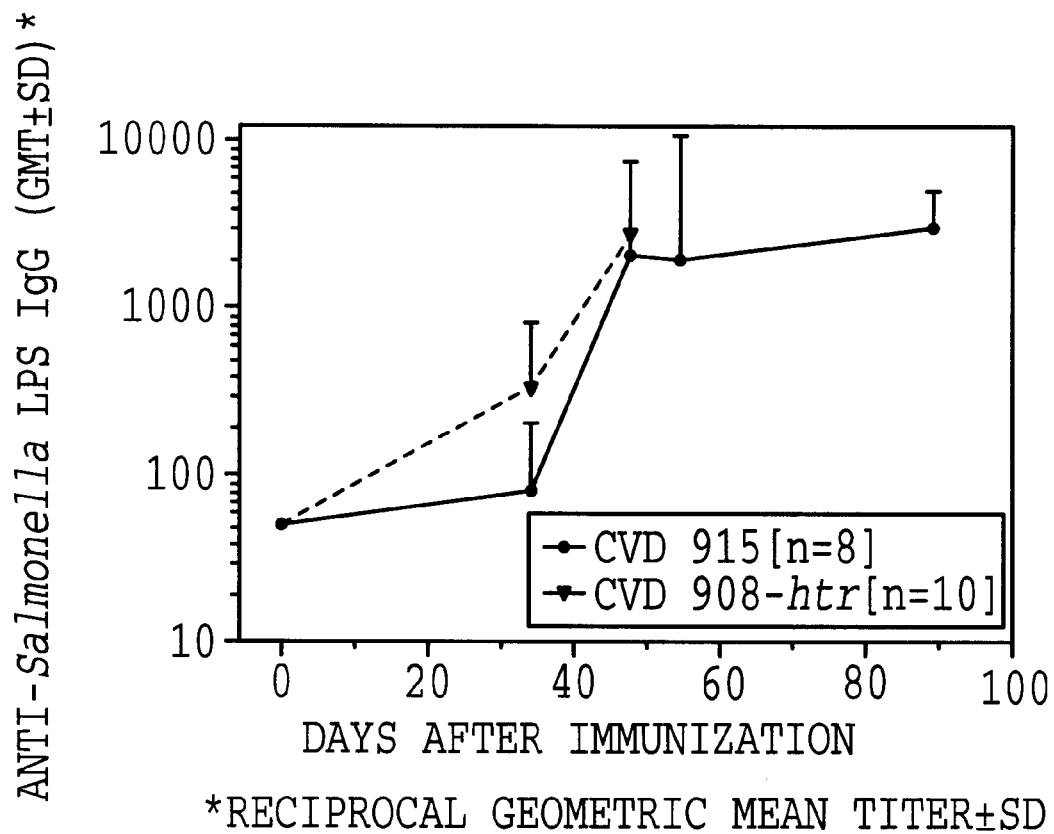
FIG. 10 shows the anti-S. typhi LPS antibody response in mice after intranasal immunization with strain ΔguaB–A S. typhi CVD 915 or strain ΔaroC, ΔaroD, ΔhtrA S. typhi CVD 908-htrA.

As shown in FIGS. 9 and 10, similar anti-Salmonella flagella and anti-Salmonella LPS antibody levels, respectively, were elicited in both animal groups.

EXAMPLE 5

Figure 1A:
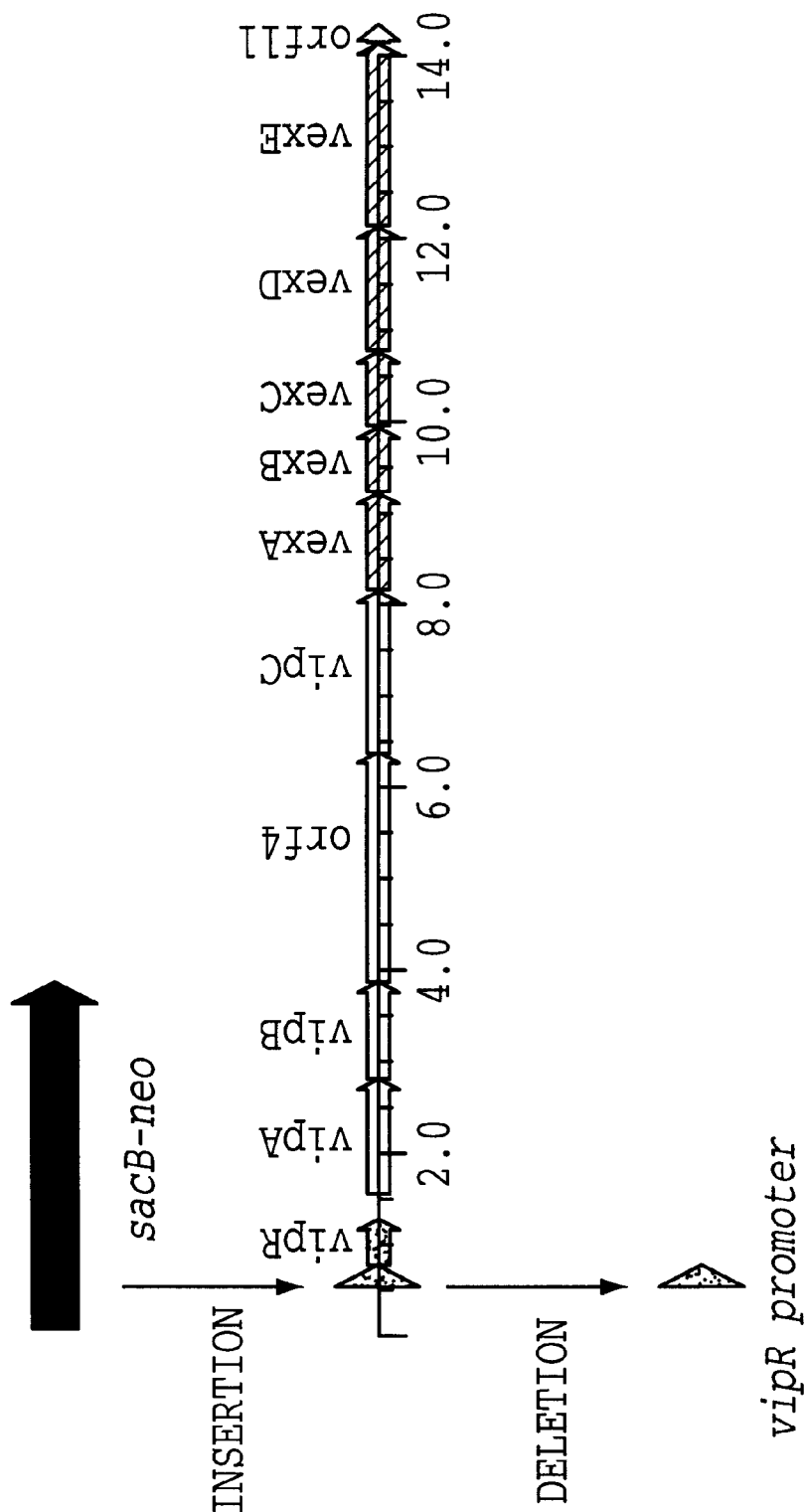
FIGS. 1A–1B shows the viaB operon; and schematically represents the exchange of the wild-type, osmotically-regulated promoter of vipR in the viaB operon by the sacB-Neo cassette (FIG. 1A); and exchange of the sacB-Neo cassette insertion by the powerful constitutive promoter $P_{tac}$, in order to make the expression of the Vi antigen constitutive (FIG. 1B).

Construction of Attenuated S. typhi Strains which Constitutively Expresses the Vi Antigen A. Construction of a S. typhi Strains (CVD 916 and CVD909)that Constitutively Express the Vi Antigen In order to change the expression of the Vi antigen from osmotically regulated to constitutive, the promoter of vipR was focused upon (FIG. 1A). It is thought that the products of vipR, and ompR-envZ perform their regulatory action by binding the upstream region of vipR (Hashimoto et al (1996), supra). To this effect, it was postulated in the present invention that by substituting the promoter of vipR with a strong promoter, e.g., $P_{tac}$, the down-regulation of vipR, and subsequently the control in the expression of the Vi antigen, would be eliminated. The promoter $P_{tac}$ is constitutive in Salmonella spp., as these organisms lack laqI. Accordingly, constitutive Vi antigen-expressor derivatives of CVD 915 and CVD 908-htrA were constructed in the following manner.

In the first phase, a deletion was introduced into vipR, and in parallel, a selection/counter-selection marker, i.e., the sacB-neo cassette, was substituted for the promoter region of vipR (FIG. 1A).

Specifically, a 601 bp segment immediately upstream of the −35 promoter region of vipR was amplified from wild-type S. typhi strain Ty2 genomic DNA, using the primers: 5'-GGGG GAGCTCAATTCTGCAAACCAGCCCTGTACCATCAA GTTCATA-3', (SEQ ID NO: 7) and 5'-CCTCAT CCCGGGCCC GGATCCACCTGCACAATTCATTGTTTGTACCTATC-3' (SEQ ID NO: 8). This first 601 bp amplified segment (segment A) was cloned using the PGEM-T Vector System kit (Promega, Madison, Wis.) giving rise to pGEM-T::fragment A. This system includes an open plasmid (pGEM-T) with 3'-T overhangs at the insertion site, which improve the efficiency of ligation of PCR products. Then, pGEM-T::segment A was digested with SstI and BamHI, and cloned into the SstI and BamHI sites immediately upstream of $P_{tac}$ in pBS: :$P_{tac}$ (this plasmid was obtained by cloning the promoter $P_{tac}$ in the BamHI-EcoRI sites of pBluescript (Stratagene)), yielding pBS::segment A-$P_{tac}$.

In parallel, a 770 bp segment of vipR (including the initiation codon of vipR) (segment B) was amplified from the same strain Ty2 genomic DNA, using the primers: 5'-GCAGGTGGATCCGGG CCCGGGATGAGGTTTCATCATTTCTGGCCTCCGAAT GATATC-3' (SEQ ID NO: 9); and 5'-ATCCTT GAATTCGGG GGATCCTACTAAAATTTTATATTTACAAAGTTAATTC TAGGT-3' (SEQ ID NO: 10). With these primers, the unique restriction sites SstI, EcoRI, BamHI and SmaI were introduced for cloning purposes (underlined). The amplified Segment B was first cloned in pGEM-T using the pGEM-T Vector System kit, yielding pGEM-T::segment B. This plasmid was then digested with EcoRV and SalI, and the resulting fragment cloned in the EcoRV and SalI sites of pBS::segment A-$P_{tac}$, immediately downstream of $P_{tac}$. The resulting plasmid, called pBS::$P_{tac}$-vipR, contains segment A-$P_{tac}$-segment B, and has a deletion of 167 bp, including the −35, −10 and ribosomal binding regions of the vipR promoter. However, in the construction of pBS::$P_{tac}$-vipR, the deletion of the vipR promoter was effectively replaced with a 257 bp insertion containing the −35, −10 and ribosomal binding regions of the tac promoter.

In parallel, other cassettes was constructed by insertion of sacB-neo between segment A and segment B referred to above. Initially, fragment A and fragment B were fused by PCR using both fragments as template and oligonucleotides SEQ ID NO: 7 and SEQ ID NO: 10 as primers, as described by Noriega et al (1996), supra. The resulting amplified fragment A-fragment B fusion was cloned in pGEM-T, using the pGEM-T Vector System kit, yielding pGEM-T::fragment A-fragment B. Then, sacB-neo was obtained by SmaI digestion of pIB729 (Blomfield et al, supra), and inserted in the SmaI site of pGEM-T::segment A-segment B. The resulting plasmid was named pGEM-T::vipR::sacB-neo. This plasmid was digested with SstI, effectively removing the vipR::sacB-neo allele, which was then cloned in the SstI site of the suicide vector pJG14, yielding pJG14::vipR::sacB-neo. pJG14 is a temperature-sensitive, pSC101 origin of replication-derived, chloramphenicol-selected, suicide plasmid (Galen et al, 96 th General Meeting, American Society for Microbiology, Abstract, page 529–H260 (1996)). In addition, the SstI-digested vipR::sacB-neo allele was cloned in the SstI site of suicide vector pKTN701 (Hone et al (1991), supra), yielding pKT::vipR::sacB-neo. S. typhi strain CVD 915 was electroporated with pJG14::vipR::sacB-neo. In parallel, S. typhi strain CVD 908-htrA was electroporated with pKT::vipR::sacB-neo. Homologous recombination was carried out between pJG14::vipR::sacB-neo and the vipR gene in S. typhi CVD 915, using the procedures described by Noriega et al (1996), supra; and between pKT::vipR::sacB-neo, and the vipR gene in S. typhi CVD 908-htrA, using the procedures described by Hone et al (1991), supra, with the exception that double cross-over mutant selection was enhanced by isolating kanamycin-resistant, chloramphenicol-sensitive clones. The resulting S. typhi CVD 915-derivative and CVD 908-htrA-derivative strains did not express the Vi antigen due to the insertion/deletion in the vipR allele.

Figure 1B:
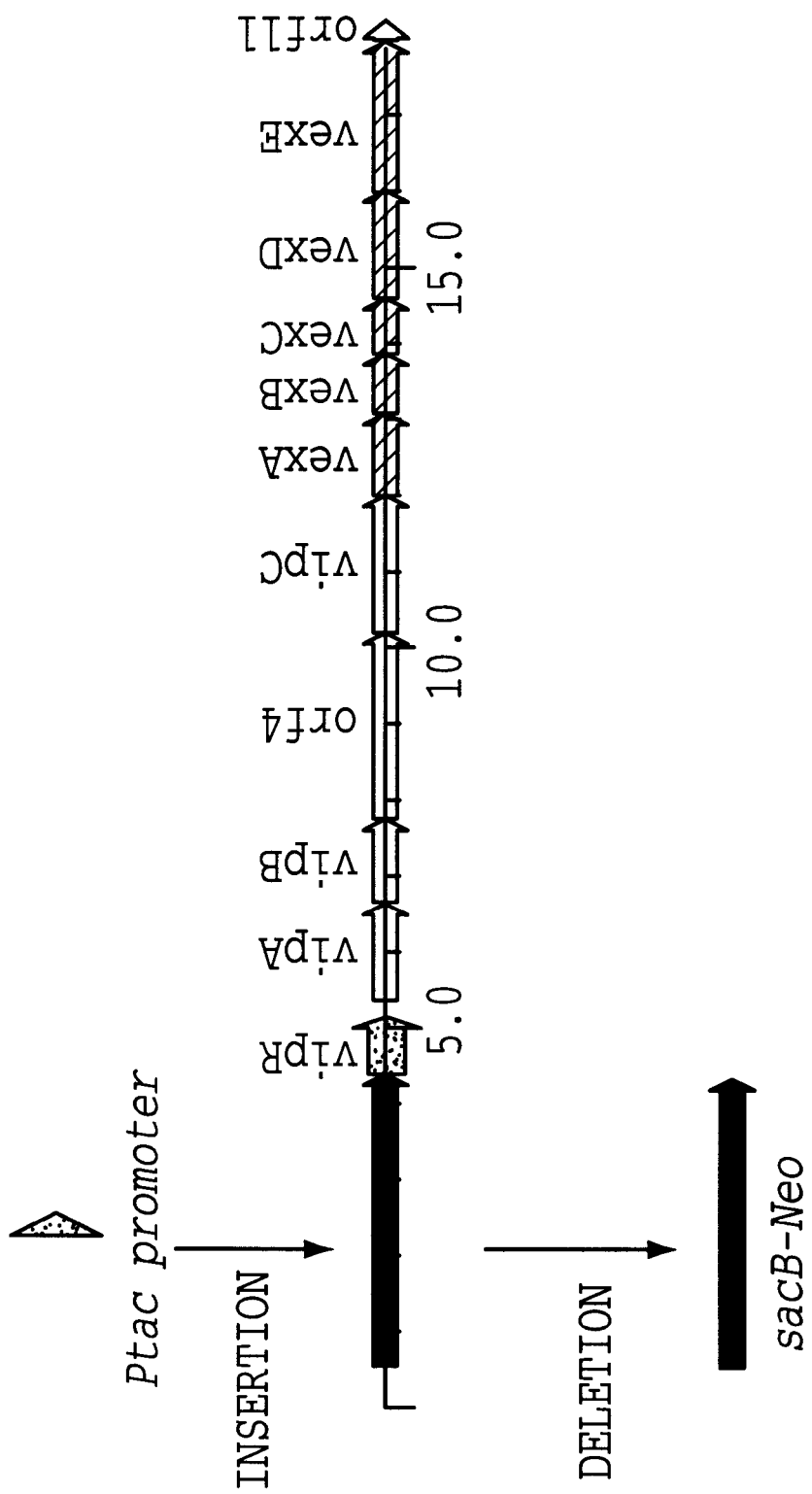

In the second phase, the constitutive $P_{tac}$ promoter was substituted for the sacB-neo insertion in the vipR locus of the S. typhi CVD 915-derivative and S. typhi CVD 908-htrA-derivative strains noted above (FIG. 1B). Specifically, the $P_{tac}$-vipR segment in pBS::$P_{tac}$-vipR was cloned into the BamHI-EcoRI site of pJG14, yielding pJG14::$P_{tac}$-vipR. Plasmid pJG14::$P_{tac}$-vipR was then used to exchange $P_{tac}$ for sacB-neo in the CVD 915- and CVD 908-htrA-derivative strains by homologous recombination, as described above. The isolation of double cross-over mutants was enhanced by the counter-selection provided by the toxicity to sucrose conferred by sacB, and reversion to kanamycin sensitivity. The resulting strain derived from CVD 915 was named CVD 916, which was deposited at the American Type Culture Collection on May 4, 1998, under ATCC No. 202116. The resulting strain derived from CVD 908—htrA was named CVD 909, which was deposited at the American Type Culture Collection on May 4, 1998, under ATCC No. 202117. Genotypically, the $P_{tac}$ insertion in both strains was characterized by PCR, demonstrating the insertion of $P_{tac}$ in the appropriate site.

B. Constitutive Expression of the Vi Antigen by Strains CVD 916 and CVD 909

Phenotypically, the constitutive expression of the Vi antigen was assessed by agglutination of bacteria grown at different osmolarities using commercial anti-Vi antiserum (Difco). The results are shown in Table 5 below.

TABLE 5

| | Agglutination with Vi-specific antiserum | | | | |
|---|---|---|---|---|---|
| | Strain | | | | |
| NaCl | CVD 915 | CVD 916 | CVD 908htrA | CVD 909 | Ty2 |
| 0.17M | +++ | ++++ | +++ | ++++ | +++ |
| 0.3M | +++ | +++ | +++ | +++ | +++ |
| 0.5M | − | +++ | +/− | +++ | − |
| 0.6M | − | +++ | − | +++ | − |
| 0.7M | − | +++ | − | +++ | − |

As shown in Table 5 above, in the wild-type S. typhi strain Ty2 and the attenuated strains CVD 915 and CVD 908—htrA, the expression of the Vi antigen is highly dependent on the osmolarity (provided by the NaCl concentration) of the medium. In contrast, the expression of the Vi antigen in strains CVD 916 and CVD 909 is strong, constitutive, and not regulated by changes in osmolarity.

EXAMPLE 6

Immune Response Against a Constitutively Expressed Vi Antigen

Groups of ten 6 weeks old Balb/c mice were immunized intranasally with $1.0 \times 10^{10}$ cfu of either strain CVD 915 or CVD 916. Mice were bled prior and 30 days after their immunization, and their serum stored at −20° C. until used. Antibodies present in the serum against S. typhi LPS, H (flagella) and Vi antigens were determined by ELISA as described by Tacket et al (1997), supra. The results are shown in Table 6 below.

TABLE 6

Geometric Mean Titers of Serum IgG Antibodies Against S. typhi Antigens After a Single Immunization with Strains CVD 915 or CVD 916

| | Specific IgG antibodies against | | | | | |
|---|---|---|---|---|---|---|
| | Vi | | LPS | | H | |
| Strain | Day 0 | Day 30 | Day 0 | Day 30 | Day 0 | Day 30 |
| CVD 915 | 21 | 46 | 19 | 640 | 20 | 197 |
| CVD 916 | 26 | 109* | 17 | 747** | 21 | 320** |

*P = 0.033
**P = Non-significant

As shown in Table 6 above, immunization with strain CVD 916 elicited antibody levels against the Vi antigen which were significantly higher than those obtained with strain CVD 915. The immune responses against other S. typhi antigens (LPS and H) were similar between both immunized groups. The results demonstrate that the constitutive expression of the Vi antigen enhances the immune response against this antigen without interfering with the immune response against other somatic S. typhi antigens.

While the invention has been described in detail, and with reference to specific embodiments thereof, it will be apparent to one of ordinary skill in the art that various changes and modifications can be made therein without departing from the spirit and scope thereof.

What is claimed:

1. An attenuated Salmonella mutant, wherein said mutant constitutively expresses Vi antigen, and wherein in said mutant, the vipR promoter is replaced by a constitutive promoter, so as to cause constitutive expression of viaB.

2. The attenuated Salmonella mutant of claim 1, wherein said mutant is a *Salmonella typhi* mutant.

3. The attenuated Salmonella mutant of claim 1 or 2, wherein in said mutant, the vipR promoter is replaced by a promoter selected from the group consisting of $P_{tac}$, $P_{trc}$, $P_{Olac}$ and $P_{lpp}$, so as to cause constitutive expression of viaB.

4. The attenuated Salmonella mutant of claim 1 or 2, wherein said mutant is incapable of forming de novo guanine nucleotides, due to mutation in the guaB–A operon.

5. The attenuated Salmonella mutant of claim 4, wherein said mutation in the guaB–A operon is a deletion mutation, and said deletion mutation is in the guaA gene, the guaB gene, or in both the guaA gene and the guaB gene.

6. The attenuated Salmonella mutant of claim 5, wherein said deletion mutation is in both the guaA gene and the guaB gene.

7. The attenuated Salmonella mutant of claim 6, wherein said mutant has an $aro^-$ phenotype.

8. The attenuated Salmonella mutant of claim 2, wherein said *Salmonella typhi* mutant is derived from parent strain *Salmonella typhi* CVD 915 (ATCC No. 202115).

9. The attenuated Salmonella mutant of claim 1, wherein said Salmonella mutant is *Salmonella typhi* CVD 916 (ATCC No. 202116) or *Salmonella typhi* CVD 909 (ATCC No. 202117).

10. The attenuated Salmonella mutant of claim 1, wherein said mutant encodes and expresses a foreign antigen.

11. The attenuated Salmonella mutant of claim 1, wherein said mutant contains a plasmid which encodes and expresses, in a eukaryotic cell, a foreign antigen.

12. A vaccine against typhoid fever comprising:

(A) a pharmaceutically effective amount of an attenuated *Salmonella typhi* mutant, wherein said mutant constitutively expresses Vi antigen, and wherein in said mutant, the vipR promoter is replaced by a constitutive promoter, so as to cause constitutive expression of viaB; and (B) a pharmaceutically acceptable carrier or diluent.

13. The vaccine of claim 12, wherein in said mutant, the vipR promoter is replaced by a promoter selected from the group consisting of $P_{tac}$, $P_{trc}$, $P_{Olac}$ and $P_{lpp}$, so as to cause constitutive expression of viaB.

14. The vaccine of claim 12 or 13, wherein said mutant is incapable of forming de novo guanine nucleotides, due to mutation in the guaB–A operon.

15. The vaccine of claim 14, wherein said mutation in the guaB–A operon is a deletion mutation, and said deletion mutation is in the guaA gene, the guaB gene, or in both the guaA gene and the guaB gene.

16. The vaccine of claim 15, wherein said deletion mutation is in both the guaA gene and the guaB gene.

17. The vaccine of claim 16, wherein said mutant has an aro⁻ phenotype.

18. The vaccine of claim 12, wherein said *Salmonella typhi* mutant is derived from parent strain *Salmonella typhi* CVD 915 (ATCC No. 202115).

19. The vaccine of claim 12, wherein said *Salmonella typhi* mutant is *Salmonella typhi* CVD 916 (ATCC No. 202116) or *Salmonella typhi* CVD 909 (ATCC No. 202117).

20. The vaccine of claim 12, wherein said mutant encodes and expresses a foreign antigen.

21. The vaccine of claim 12, wherein said mutant contains a plasmid which encodes and expresses, in a eukaryotic cell, a foreign antigen.

22. The vaccine of claim 12, wherein said pharmaceutically effective amount is about $10^2$ cfu to $10^{10}$ cfu.

23. The vaccine of claim 22, wherein said pharmaceutically effective amount is about $10^6$ cfu to $10^9$ cfu.

* * * * *